(12) United States Patent
Ambrosini et al.

(10) Patent No.: US 10,400,285 B2
(45) Date of Patent: Sep. 3, 2019

(54) DDX43 AS A BIOMARKER OF RESISTANCE TO MEK1/2 INHIBITORS

(71) Applicant: Memorial Sloan-Kettering Cancer Center, New York, NY (US)

(72) Inventors: Grazia Ambrosini, Astoria, NY (US); Raya Khanin, New York, NY (US); Richard Carvajal, New York, NY (US); Gary K. Schwartz, Briarcliff Manor, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 0 days.

(21) Appl. No.: 15/061,578

(22) Filed: Mar. 4, 2016

(65) Prior Publication Data
US 2016/0258027 A1    Sep. 8, 2016

Related U.S. Application Data

(63) Continuation of application No. PCT/US2014/054263, filed on Sep. 5, 2014.

(60) Provisional application No. 61/874,218, filed on Sep. 5, 2013.

(51) Int. Cl.
| | | |
|---|---|---|
| *C12Q 1/6886* | (2018.01) | |
| *A61K 31/4184* | (2006.01) | |
| *A61K 31/4375* | (2006.01) | |
| *G01N 33/574* | (2006.01) | |

(52) U.S. Cl.
CPC ........ *C12Q 1/6886* (2013.01); *A61K 31/4184* (2013.01); *A61K 31/4375* (2013.01); *G01N 33/5743* (2013.01); *C12Q 2600/106* (2013.01); *C12Q 2600/136* (2013.01); *C12Q 2600/158* (2013.01); *G01N 2333/914* (2013.01)

(58) Field of Classification Search
None
See application file for complete search history.

(56) References Cited

U.S. PATENT DOCUMENTS

2011/0158944 A1    6/2011    Hosted et al.

FOREIGN PATENT DOCUMENTS

| WO | WO 2008/100913 A2 | 8/2008 |
| WO | WO 2011/094233 A1 | 8/2011 |
| WO | WO 2012/119113 A2 | 9/2012 |
| WO | WO 2012/135779 A1 | 10/2012 |

OTHER PUBLICATIONS

Gaitonde et al., "BI-69A11-mediated inhibition of AKT leads to effective regression of xenograft melanoma", Pigment Cell & Melanoma Research, 2009, vol. 22(2), pp. 187-195.*
Abdelhaleem, "Over-expression of RNA Helicases in Cancer," Anticancer Research 24:3951-3954 (2004).
Adams et al., "Frequent expression of HAGE in presentation chronic myeloid leukaemias," Leukemia 16:2238-2242 (2002).
Adjei et al., "Phase I Pharmacokinetic and Pharmacodynamic Study of the Oral, Small-Molecule Mitogen-Activated Protein Kinase Kinase 1/2 Inhibitor AZD6244 (ARRY-142886) in Patients With Advanced Cancers," J Clin Oncol 26(13):2139-2146 (2008).
Ambrosini et al., "Identification of unique MEK-dependent genes in GNAQ mutant uveal melanoma involved in cell growth, tumor cell invasion, and MEK-resistance," Clin Cancer Res. 18(13):3552-3561 (2012).
Ambrosini et al., "Inhibition of Mutant GNAQ Signaling in Uveal Melanoma Induces AMPK-Dependent Autophagic Cell Death," Mol Cancer Ther 12(5):768-776 (2013).
Ambrosini et al., "Overexpression of DDX43 Mediates MEK Inhibitor Resistance Through RAS Upregulation in Uveal Melanoma Cells," Mol. Cancer Ther. 13(8):2073-2080 (Aug. 2014).
Anders et al., "Differential expression analysis for sequence count data," Genome Biology 11:R106 (2010).
Bennouna et al., "A Phase II, open-label, randomised study to assess the efficacy and safety of the MEK1/2 inhibitor AZD6244 (ARRY-142886) versus capecitabine monotherapy in patients with colorectal cancer who have failed one or two prior chemotherapeutic regimens," Invest New Drugs 29:1021-1028 (2011).
Bhattacharya et al., "The DEAD/DEAH box helicase, DDX11, is essential for the survival of advanced melanomas," Mol Cancer 11:82 (2012).

(Continued)

*Primary Examiner* — Savitha M Rao
*Assistant Examiner* — Gregg Polansky
(74) *Attorney, Agent, or Firm* — Baker Botts L.L.P.

(57) ABSTRACT

The present invention relates to methods and compositions for determining the likelihood that a subject suffering from a cancer will benefit from treatment with a MEK inhibitor. It also relates to methods of treatment based on such determination. The invention is based, at least in part, on the discoveries that DDX43 mRNA and protein are expressed at high levels in biopsies from "non-responder" UM patients and that selumetinib-resistant cell lines showed high DDX43 expression which correlated with increased expression and activity of RAS. It was found that KRAS and HRAS but not NRAS, mediated expression of pERK and pAKT, bypassing oncogenic GNAQ. The invention is further based on the discovery that selumetinib-resistant cells became sensitive to AKT inhibition, suggesting alternative strategies for the treatment of cancer patients with acquired resistance to MEK inhibitors.

6 Claims, 16 Drawing Sheets

(56) References Cited

OTHER PUBLICATIONS

Figure 1A:
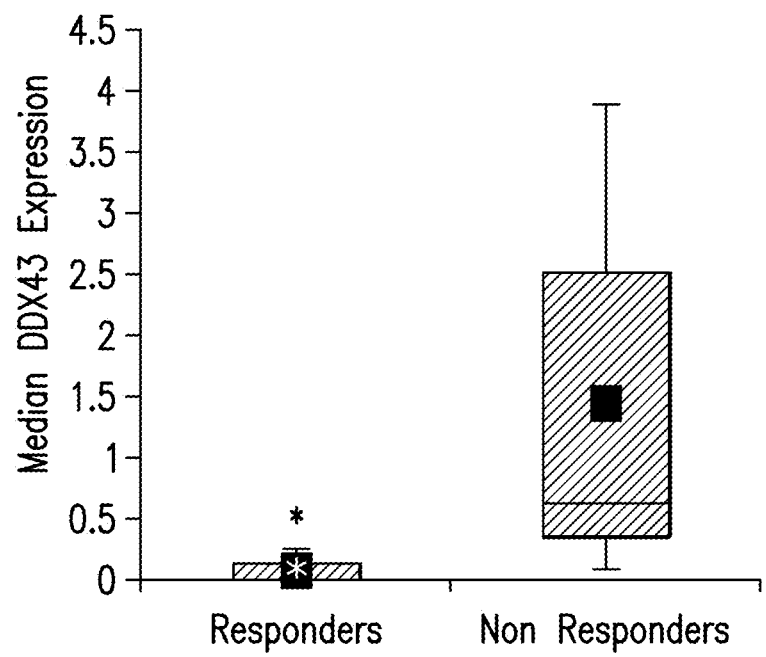

Camats et al., "P68 RNA Helicase (DDX5) Alters Activity of Cis- and Trans-acting Factors of the Alternative Splicing of H-Ras," PLoS One 3(8):e2926 (2008).
Carvajal et al., "Pharmacodynamic activity of selumetinib to predict radiographic response in advanced uveal melanoma," J Clin Oncol 30 ((suppl; abstr 8598)) (2012).
Chan et al., "HAGE (DDX43) protein expression as an independent biomarker of poor clinical outcome of breast cancer (BC) and potential as a therapeutic target for ER-negative BC," J Clin Oncol 30 (suppl; abstr 1013) (2012).
Chen et al., "Aberrant hypomethylation of DDX43 promoter in myelodysplastic syndrome," Br. J. of Haematology 158:283-296 (2012).
Corcoran et al., "BRAF Gene Amplification Can Promote Acquired Resistance to MEK Inhibitors in Cancer Cells Harboring the BRAF V600E Mutation," Science Signaling 3(149):ra84 (2010).
Edelhauser et al., "Fotemustine Chemoembolization of Hepatic Metastases From Uveal Melanoma: A Retrospective Single-Center Analysis," AJR 199:1387-1392 (2012).
Emery et al., "MEK1 mutations confer resistance to MEK and B-RAF inhibition," PNAS 106(48):20411-20416 (2009).
Fuller-Pace, "DExD/H box RNA helicases: multifunctional proteins with important roles in transcriptional regulation," Nucleic Acids Res 34(15):4206-4215 (2006).
GenBank Accesion No. NM_ 018665, Homo sapiens DEAD (Asp-Glu-Ala-Asp) box polypeptide 43 (DDX43), Mrna (accessed on Nov. 22, 2016).
GenBank Accession No. NM 001191044.1 (accessed on Nov. 22, 2016).
GenBank Accession No. NP 001177973.1 (accessed on Nov. 22, 2016).
GenBank Accession No. NP 061135.2 (accessed on Nov. 22, 2016).
GenBank Accession No. XM 003986327 (accessed on Nov. 22, 2016).
GenBank Accession No. XM 518584.3 (accessed on Nov. 22, 2016).
GenBank Accession No. XM 848647.2 (accessed on Nov. 22, 2016).
GenBank Accession No. XP 003986376.1 (accessed on Nov. 22, 2016).
GenBank Accession No. XP 518584.2 (accessed on Nov. 22, 2016).
GenBank Accession No. XP 853740.1 (accessed on Nov. 22, 2016).
Gopal et al., "Basal and Treatment-Induced Activation of AKT Mediates Resistance to Cell Death by AZD6244 (Arry-142886) in Braf-Mutant Human Cutaneous Melanoma Cells," Cancer Res 70(21):8736-8747 (2010).
Gragoudas et al., "Survival of Patients with Metastases from Uveal Melanoma," Ophthalmology 98(3):383-389; discussion 390 (1991).
International Search Report dated Feb. 25, 2015 in International Application No. PCT/US14/54263.
Jarmoskaite et al., "DEAD-box proteins as RNA helicases and chaperones," WIREs RNA 2(1):135-152 (2011).
Karnoub et al., "Ras oncogenes: split personalities," Nat Rev Mol Cell Biol 9:517-531 (2008).
Kath et al., "Prognosis and Treatment of Disseminated Uveal Melanoma," Cancer 72(7):2219-2223 (1993).

Linder et al., "From unwinding to clamping—the DEAD box RNA helicase family," Nat Rev Mol Cell Biol 12:505-516 (2011).
Linley et al., "The Helicase HAGE Expressed by Malignant Melanoma-Initiating Cells Is Required for Tumor Cell Proliferation in Vivo," J Biol Chem 287(17):13633-13643 (2012).
Lito et al., "Relief of Profound Feedback Inhibition of Mitogenic Signaling by RAF Inhibitors Attenuates Their Activity in BRAFV600E Melanomas," Cancer Cell 22:668-682 (2012).
Little et al., "Amplification of the Driving Oncogene, KRAS or BRAF, Underpins Acquired Resistance to MEK1/2 Inhibitors in Colorectal Cancer Cells," Science Signaling 4(166):ra17 (2011).
Little et al., "Mechanisms of acquired resistance to ERK1/2 pathway inhibitors," Oncogene 32:1207-1215 (2013).
Martelange et al., "Identification on a Human Sarcoma of Two New Genes with Tumor-specific Expression," Cancer Res 60:3848-3855 (2000).
Mathieu et al., "HAGE, a cancer/testis antigen expressed at the protein level in a variety of cancers," Cancer Immunity 10:2 (2010).
Mathieu et al., "HAGE, a cancer/testis antigen with potential for melanoma immunotherapy: identification of several MHC class I/II HAGE-derived immunogenic peptides," Cancer Immunol Immunother 56:1885-1895 (2007).
O'Neil et al., "Phase II Study of the Mitogen-Activated Protein Kinase 1/2 Inhibitor Selumetinib in Patients With Advanced Hepatocellular Carcinoma," J Clin Oncol 29(17):2350-2356 (2011).
Onken et al., "Oncogenic mutations in GNAQ occur early in uveal melanoma," Invest Ophthalmol Vis Sci. 49(12):5230-5234 (2008).
Poulikakos et al., "RAF inhibitor resistance is mediated by dimerization of aberrantly spliced BRAF (V600E)," Nature 480(7377):387-390 (2011).
Poulikakos et al., "Resistance to MEK Inhibitors: Should We Co-Target Upstream?" Science Signaling 4(166):pe16 (2011).
Robert et al., "Perturbations of RNA helicases in cancer," WIREs RNA 4:333-349 (2013).
Roman-Gomez et al., "Epigenetic regulation of human cancer/testis antigen gene, HAGE, in chronic myeloid leukemia," Haematologica 92:153-162 (2007).
Trapnell et al., "Transcript assembly and quantification by RNA-Seq reveals unannotated transcripts and isoform switching during cell differentiation," Nat Biotechnol 28(5):511-515 (2010).
Umate et al., "Genome-wide comprehensive analysis of human helicases," Communicative & Integrative Biology 4(1):118-137 (2011).
Van Raamsdonk et al., "Frequent somatic mutations of GNAQ in uveal melanoma and blue nevi," Nature 457(7229):599-602 (2009).
Yamamoto et al., "Ras-Induced Transformation and Signaling Pathway," J. Biochem. 126:799-803 (1999).
Yonekawa et al., "Epidemiology and Management of Uveal Melanoma," Hematol Oncol Clin N Am 26:1169-1184 (2012).
Abdel-Fatah et al., "HAGE (DDX43) Protein Expression is a Powerful Independent Biomarker of Poor Clinical Outcome of Breast Cancer (BC) and Could be a Potential Therapeutic Target for ER Negative BC," Journal of Pathology 228(1):S11 (2012).
Morris et al., "Alternative Cleavage and Polyadenylation during Colorectal Cancer Development," Clinical Cancer Research 18(19):5256-5266 (2012).
Regad, "Molecular and cellular pathogenesis of melanoma initiation and progression," Cell. Mol. Life Sci. 70:4055-4065 (2013).
Supplementary European Search Report dated Feb. 27, 2017 in EP Application No. 14842562.

* cited by examiner

DDX43 AS A BIOMARKER OF RESISTANCE TO MEK1/2 INHIBITORS

CROSS-REFERENCE TO RELATED APPLICATIONS

This application is a continuation of International Patent Application No. PCT/US2014/054263, filed Sep. 5, 2014, which claims priority to U.S. Provisional Patent Application Ser. No. 61/874,218, filed Sep. 5, 2013, the contents of each of which are incorporated by reference in their entirety, and to each of which priority is claimed.

GRANT INFORMATION

This invention was made with government support under CM062206 awarded by the National Cancer Institute of the National Institutes of Health. The government has certain rights in the invention.

1. INTRODUCTION

The present invention relates to methods and kits for determining the likelihood that a subject suffering from a cancer will benefit from treatment with a MEK inhibitor based on whether or not DDX43 is over-expressed. It further relates to methods of treatment based on such determination.

2. BACKGROUND OF THE INVENTION

The prognosis of patients with metastatic uveal melanoma ("UM") is poor with a median 1-year survival rate of less than 30% [1] [2]. In 87% of patients, metastasis will develop primarily in the liver, and there are limited therapeutic options for this disease [3] [4]. Activating mutations in G-protein alpha subunits GNAQ or GNA11 are early oncogenic events in UM development [5] and result in the activation of the MAPK pathway [6]. We have reported that the small molecule MEK inhibitor selumetinib can inhibit pERK and cyclin D1, resulting in decreased viability of UM cell lines [7]. Furthermore, in patients with UM, selumetinib can result in tumor shrinkage, and the sustained inhibition of pERK may be predictive of benefit [8].

MEK inhibitors have been reported to give a partial or stable response in tumors with activated MAPK pathway, including melanoma and solid malignancies [9], [10] [11]. However, the use of small molecule MEK inhibitors has been undermined by acquired drug resistance [12], which reduces the efficacy of these drugs in the clinical setting (patients resistant to the drug being "non-responders"). For example, resistance to selumetinib has been described in colorectal cancer cells carrying BRAF and RAS mutations, where resistance is mediated by the amplification of the driving oncogene [13] [14]. In cutaneus melanoma, MEK1 mutations have been found to confer resistance to MEK inhibitors [15]. In uveal melanoma with GNAQ mutations, the mechanisms of acquired resistance have been elusive and more effective therapies are needed for the treatment of this disease.

The RNA helicase DDX43 was first identified as a cancer/testis antigen, and it is highly expressed in many tumor types compared to normal tissues [16, 52], including melanoma [19]. In particular, DDX43 was found to be overexpressed in 50% acute myeloid leukemias (CML) [17], and its expression is associated with advanced disease and poor prognosis [18]. It has been reported that DDX43 promoted expression of RAS protein through RNA unwinding [20].

DDX43, also called HAGE, is a member of the DEAD-box family of ATP-dependent RNA helicases. These proteins browse RNA molecules and promote the dissociation of the RNA from ribonucleoproteins to which they have high affinity [21]. In this way RNA helicases support processes like transcription, pre-mRNA splicing, translation initiation/elongation, and RNA degradation [22] [23]. Their altered expression levels have been also implicated in tumor initiation, progression and maintenance [24].

3. SUMMARY OF THE INVENTION

The present invention relates to methods and compositions for determining the likelihood that a subject suffering from a cancer will benefit from treatment with a MEK inhibitor. It also relates to methods of treatment based on such determination. The invention is based, at least in part, on the discoveries that DDX43 mRNA and protein are expressed at high levels in biopsies from "non-responder" UM patients and that selumetinib-resistant cell lines showed high DDX43 expression which correlated with increased expression and activity of RAS. It was found that KRAS and HRAS but not NRAS, mediated expression of pERK and pAKT, bypassing oncogenic GNAQ. The invention is further based on the discovery that selumetinib-resistant cells became sensitive to AKT inhibition, suggesting alternative strategies for the treatment of cancer patients with acquired resistance to MEK inhibitors.

4. BRIEF DESCRIPTION OF THE FIGURES

Figure 1B:
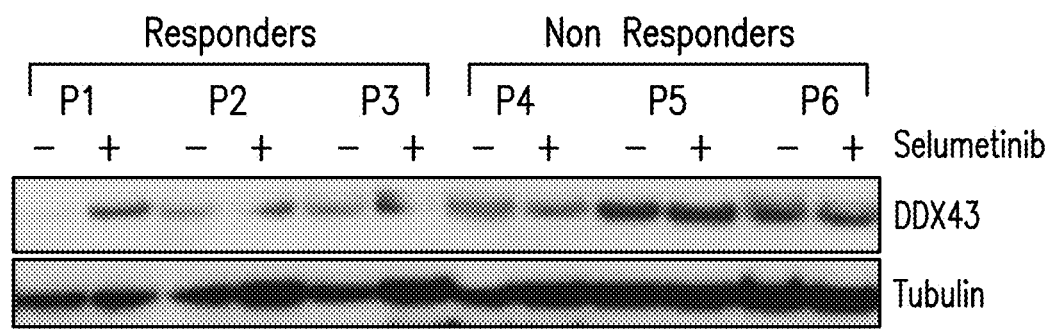

FIG. 1A and FIG. 1B. DDX43 is highly expressed at the mRNA and protein levels in "non responder" biopsies. FIG. 1A, DDX43 expression was confirmed by real-time PCR in biopsies of 14 patients before selumetinib treatment. Triplicate values were normalized with GADPH as housekeeping gene using the AACT method, and reported as a Box plot showing significant association with poor outcome in patients with uveal melanoma treated with selumetinib *p=0.045. FIG. 1B, DDX43 expression was analyzed by immunoblotting in liver biopsies of six representative patients (P) before (−) and after (+) 14 days of selumetinib treatment.

FIG. 2A-FIG. 2D. UM cells become resistant to MEK inhibition after long exposure to selumetinib. After continuous exposure, the cell lines Res-Omm1.3 (FIG. 2A) and Res-Mel270 (FIG. 2B) became resistant to selumetinib compared to their parental cell lines Omm1.3 and Mel270. Cell viability on day 4 was calculated as percent of untreated controls. Each point is a mean±sd. Immunoblot analysis of parental and resistant Omm1.3 (FIG. 2C) and Mel270 (FIG. 2D) cells treated with increasing concentrations of selumetinib for 24 hours. Both MEKi-resistant cell lines Res-Omm1.3 and Res-Mel270 showed sustained expression of pAKT, pRB, c-Jun, DDX43 and RAS, independently of treatment.

Figure 3A:
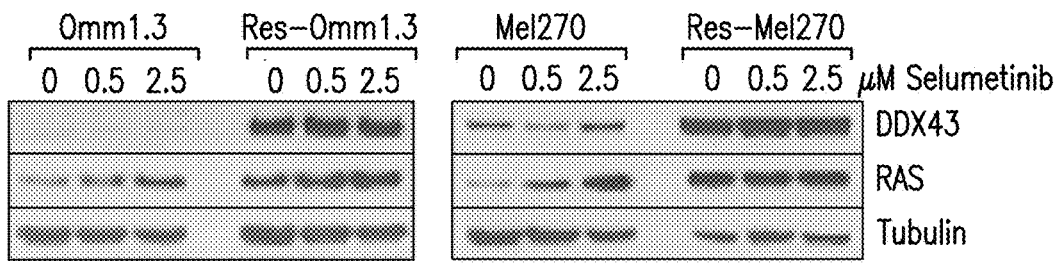
Figure 3B:
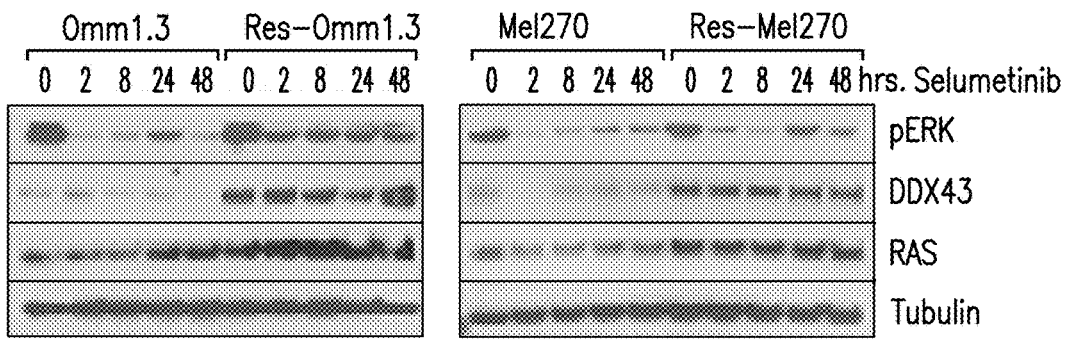
Figure 3C:
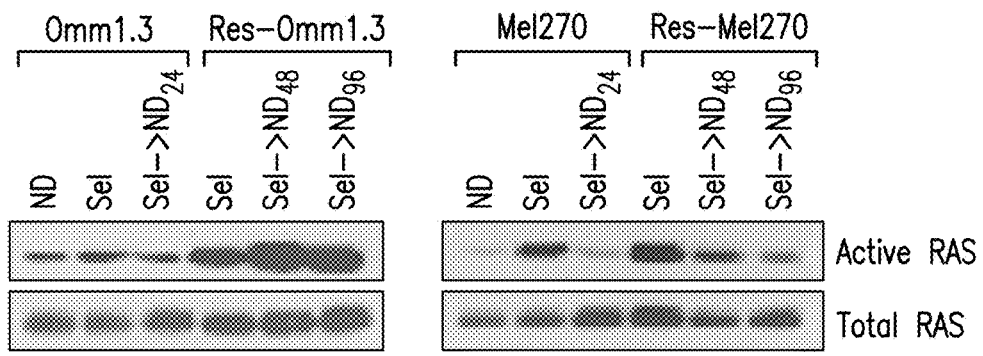

FIG. 3A-FIG. 3C. DDX43 and RAS are highly expressed in the MEKi-resistant cells. FIG. 3A, Parental and resistant cells were treated with selumetinib for up to 48 hrs and analyzed for DDX43 expression. FIG. 3B, Resistant cells were transfected with an siRNA control (−) and a DDX43-specific siRNA (+). Cell lysates were analyzed by immunoblotting for expression of DDX43, total RAS, pERK, pAKT and tubulin. FIG. 3C, Resistant cells with downregulated DDX43 were assayed in cell viability assays, after 3 days from transfection.

Figure 4A:
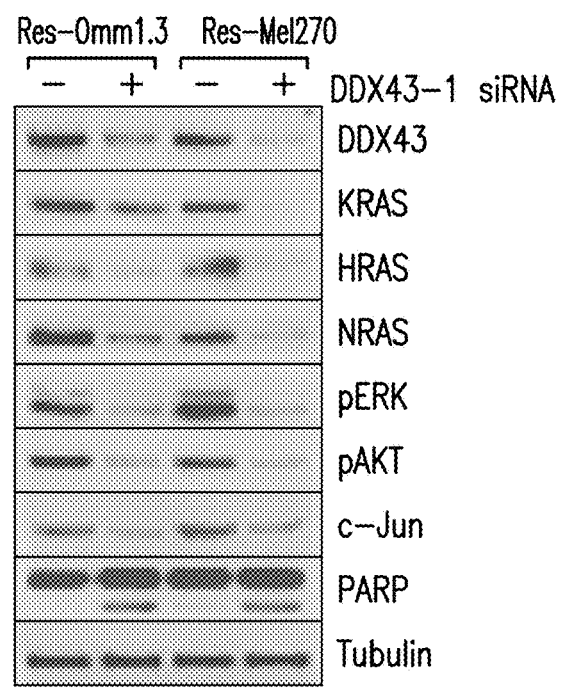
Figure 4B:
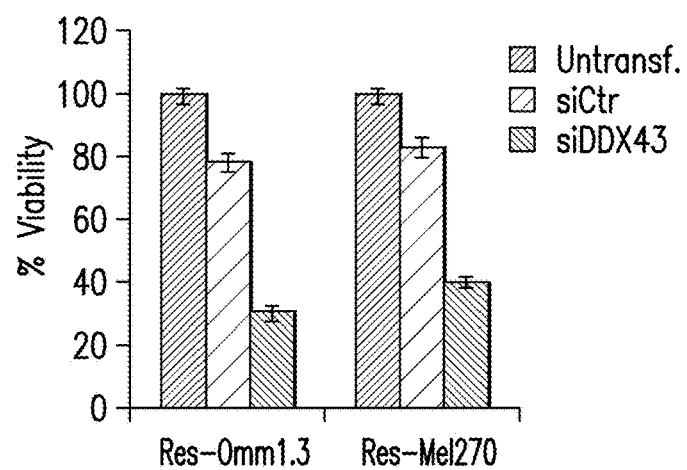
Figure 4C:
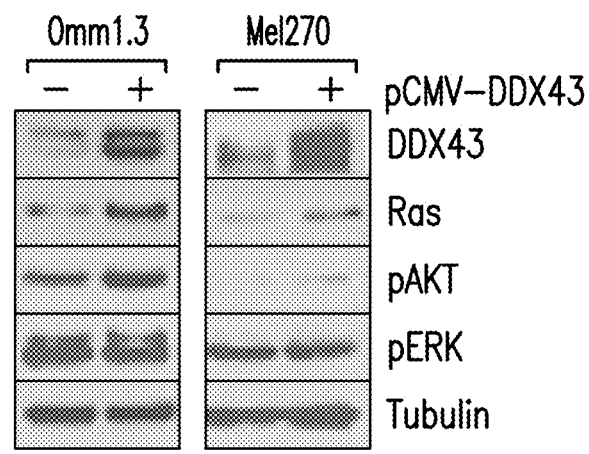
Figure 4D:
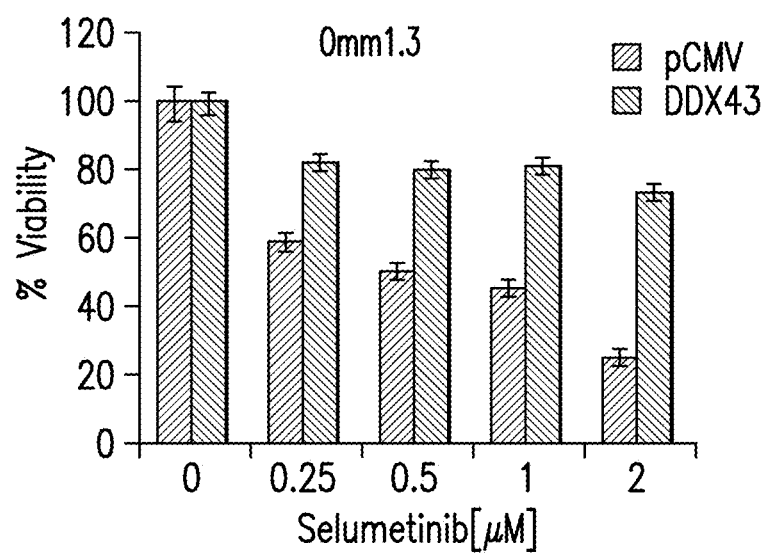

FIG. 4A-FIG. 4D. DDX43 regulates RAS expression and mediates MEK resistance. FIG. 4A, siRNA mediated knockdown of DDX43 (+) and control siRNA (−) in the MEKi-resistant cell lines downregulates KRAS, HRAS, NRAS and downstream signaling molecules like pERK, pAKT and c-Jun. FIG. 4B, Cell viability of Res-Omm1.3 and Res-Me170 was measured after 4 days from siRNA transfection. FIG. 4C, The parental cell lines Omm1.3 and Mel270 were transfected with DDX43 or the empty vector pCMV. Cell lysates were subjected to Western blot analysis for expression of RAS, pERK and pAKT. FIG. 4D, The parental cell line Omm1.3 overexpressing DDX43 is more resistant to selumetinib treatments. Columns, mean of three independent experiments.

FIG. 5A-FIG. 5D. KRAS and HRAS, but not NRAS, mediate ERK/AKT signaling in MEKi-resistant cells. Parental and MEK-resistant cells where transfected with KRAS (FIG. 5A), HRAS (FIG. 5B), NRAS (FIG. 5C) and GNAQ (FIG. 5D) siRNA and analyzed for pMEK, pERK, pAKT, c-Jun, and cyclin D1 expression by immunoblotting.

Figure 6A:
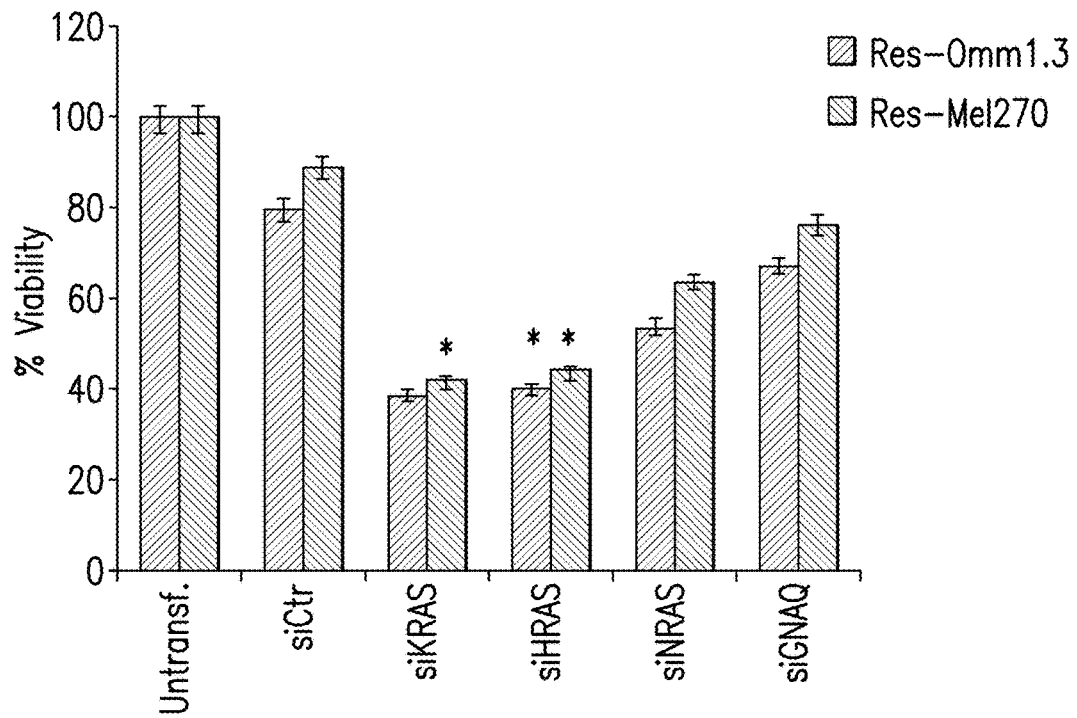
Figure 6B:
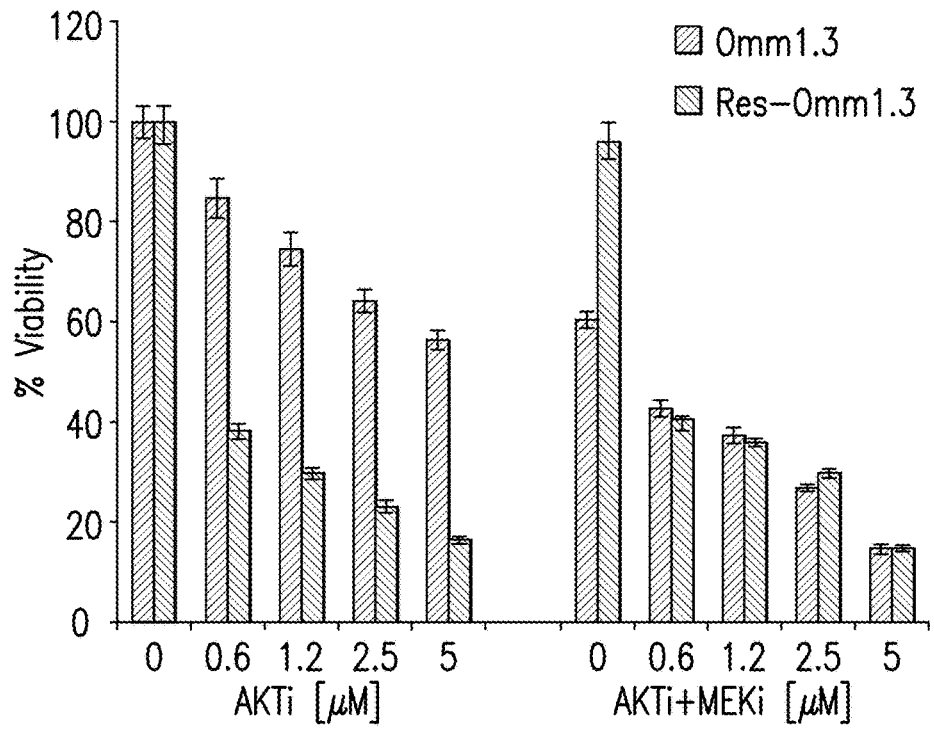
Figure 6C:
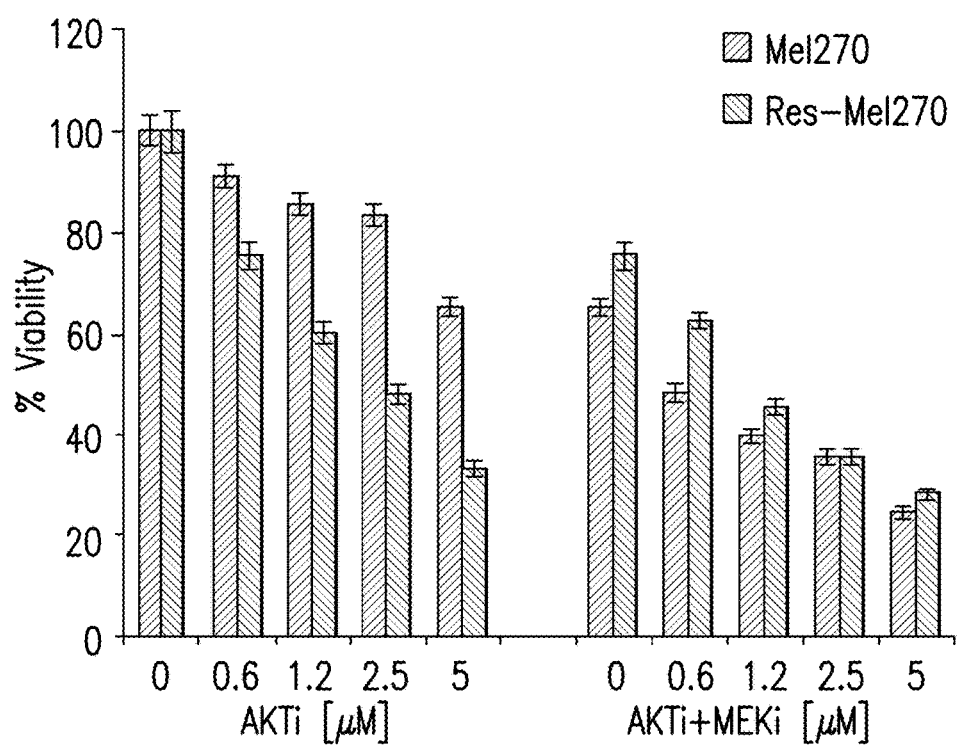
Figure 7A:
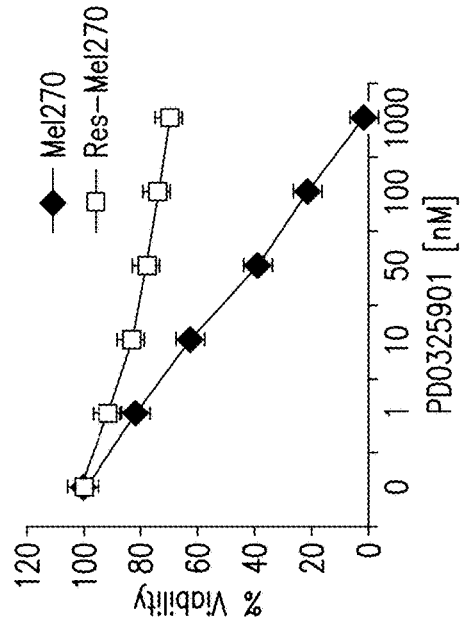
Figure 7B:
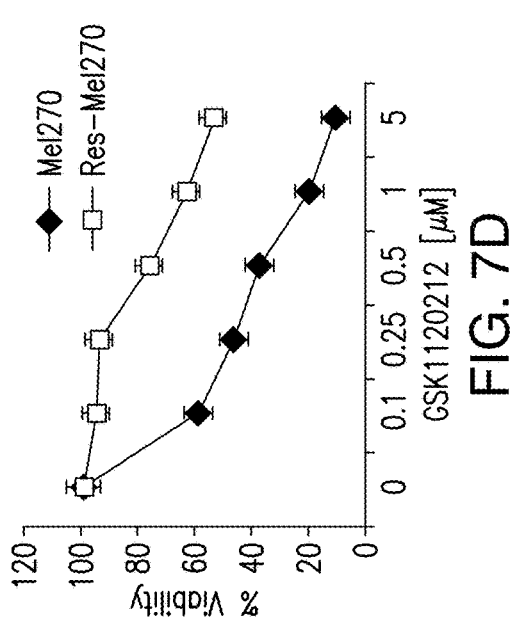
Figure 7C:
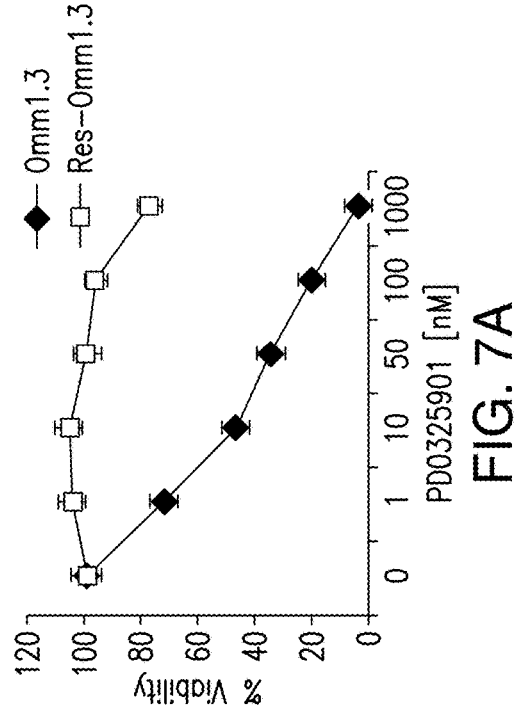
Figure 7D:
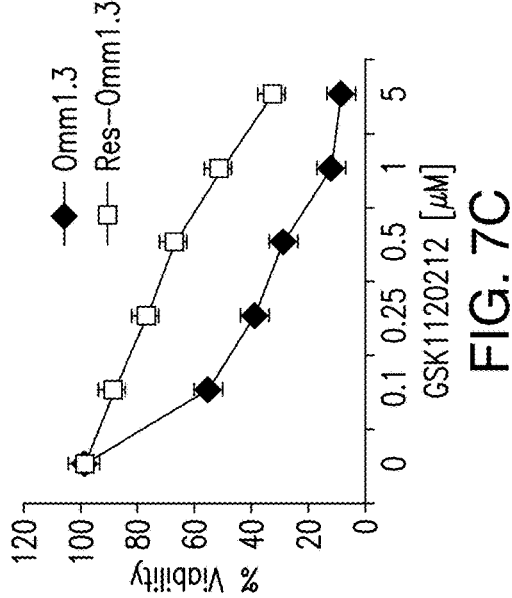

FIG. 6A-FIG. 6C. KRAS and HRAS are necessary for MEKi-resistant cells survival. The cells depleted of each RAS protein or GNAQ were tested in viability assays after 72 hr from siRNA transfection in Res-Omm1.3 (FIG. 6A) and Res-Me1270 (FIG. 6B). *p<0.0001 and **p<0.001 for comparison of siKRAS and siHRAS versus control siRNA in both cell lines. FIG. 6B and FIG. 6C, Res-Omm1.3 and Res-Me270 cells are sensitive to AKT inhibition. Sensitive and MEKi-resistant cells were exposed to increasing concentrations of MK2206 with or without selumetinib and analyzed in viability assays. Columns, mean of three independent experiments. Mean±sd FIG. 7A-FIG. 7D. Resistant and parental cell lines were treated with increasing doses of the MEK inhibitors PD0325901 (FIG. 7A, FIG. 7B) and GSK1120212 (FIG. 7C, FIG. 7D) for 4 days, and analyzed in cell viability assays. Each experiment is representative of three independent experiments. Mean±sd.

Figure 8A:
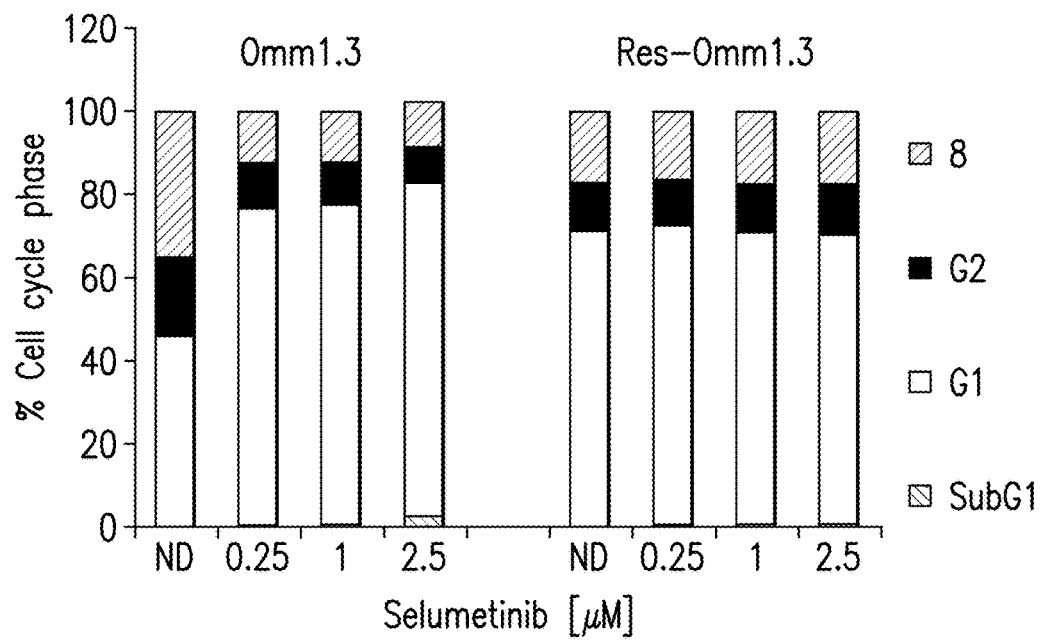
Figure 8B:
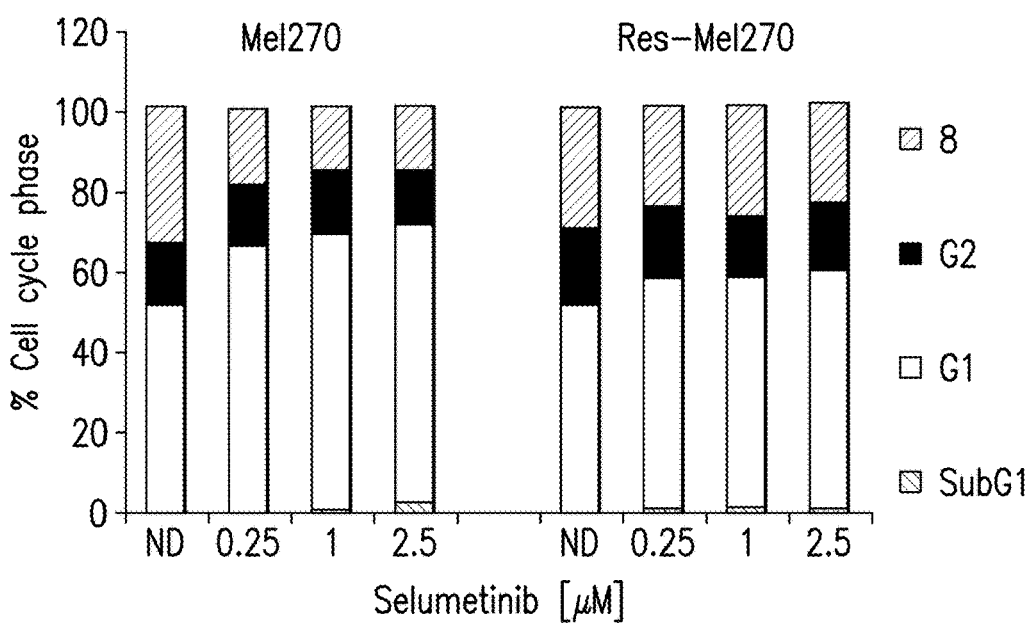

FIG. 8A-FIG. 8B. The resistant cells Res-Omm1.3 (FIG. 8A) and Res-Me1270 (FIG. 8B) escaped the G1 cell cycle arrest mediated by selumetinib after 24 hours of treatment.

Figure 9A:
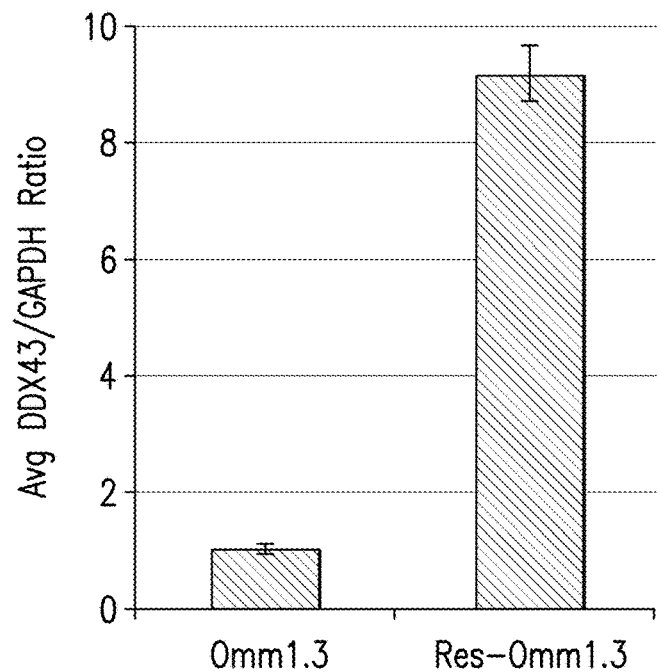
Figure 9B:
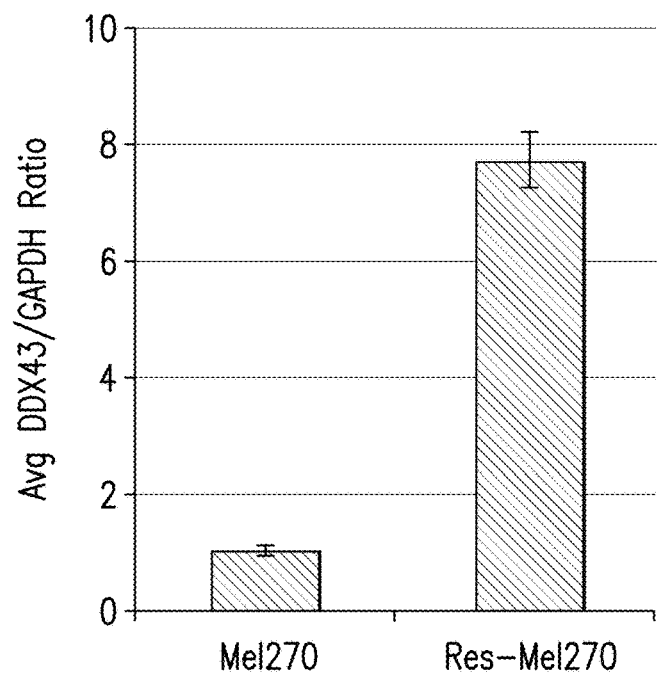

FIG. 9A-FIG. 9B. DDX43 mRNA expression is elevated in the selumetinib-resistant cells compared to their parental cells. Real-time PCR of sensitive and resistant cells (FIG. 9A) Omm1.3 and (FIG. 9B) Mel270. Triplicate values were normalized to GADPH. Mean±sd.

Figure 10:
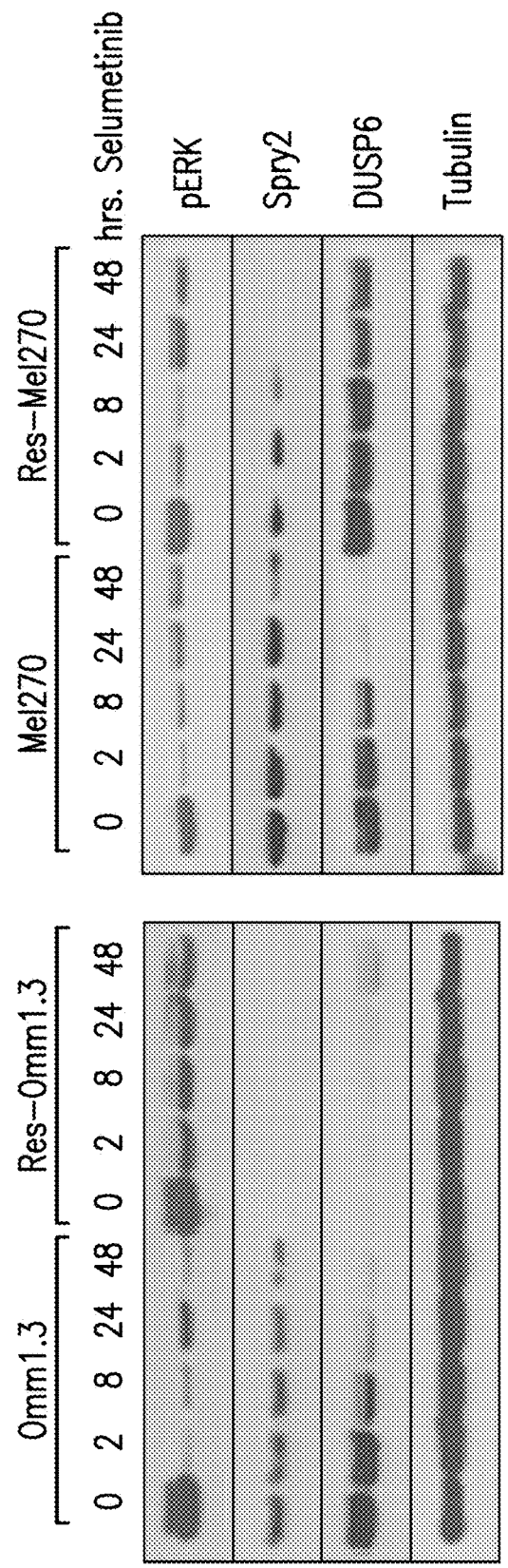

FIG. 10. Parental and MEK inhibitor-resistant cell lines were treated with selumetinib over the time. Immunoblots show the expression levels of pERK, Spry2, Dusp6 and tubulin.

Figure 11:
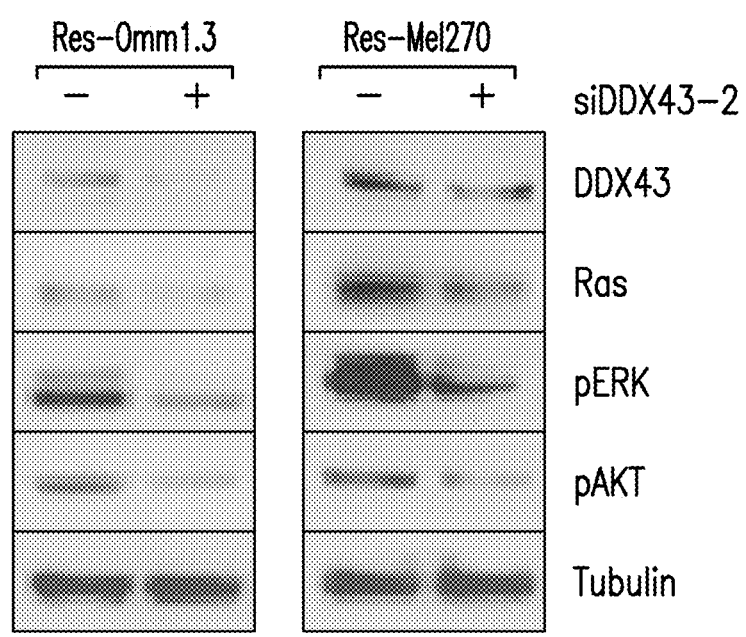

FIG. 11. A, MEKi-resistant cells were transfected with control (−) and a DDX43-2 specific (+) siRNA as in Material and Methods. After 48 hours, cell lysates were used in Western blots for the expression of DDX43, pan-RAS, pERK pAKT and tubulin.

Figure 12A:
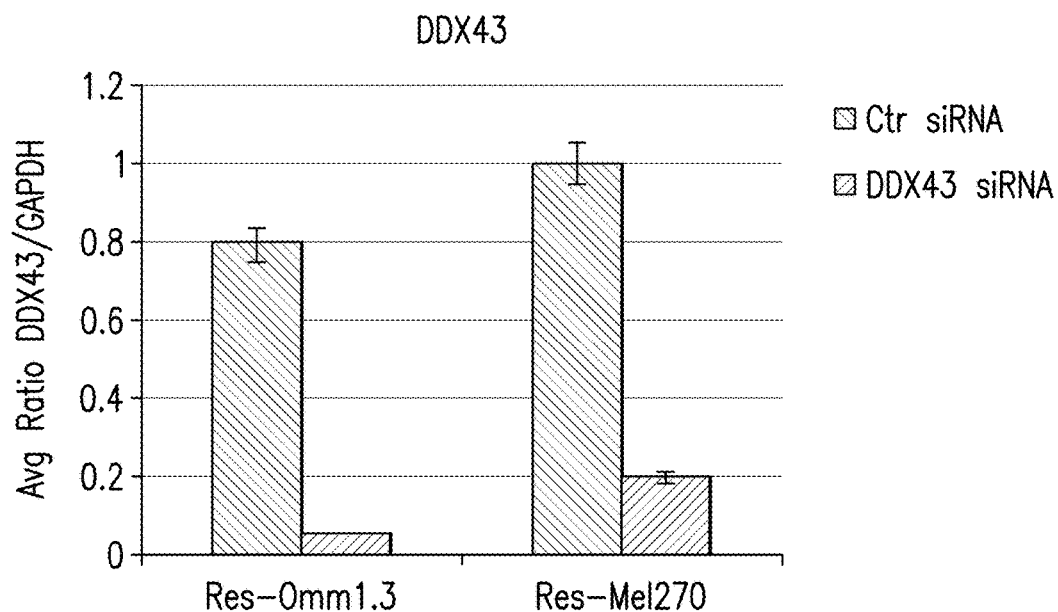
Figure 12B:
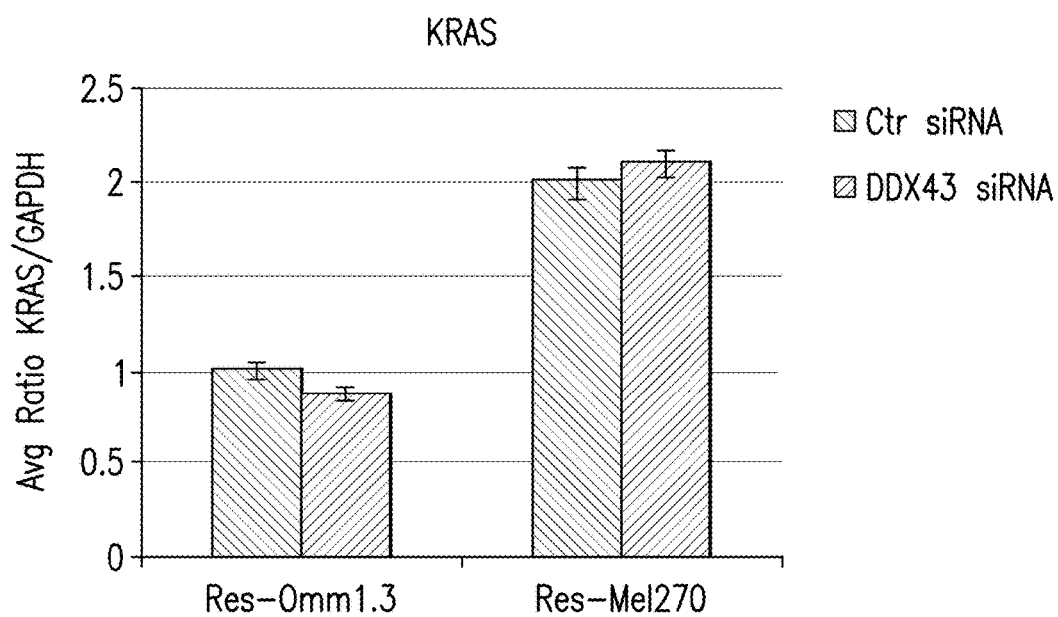

FIG. 12A-FIG. 12B. DDX43 does not regulate KRAS transcription. The resistant cells were transfected with control and DDX43 siRNA and real-time PCR for DDX43 (FIG. 12A) and KRAS (FIG. 12B) expression were performed. Triplicate values were normalized to GADPH. Mean±sd.

5. DETAILED DESCRIPTION OF THE INVENTION

For clarity of disclosure and not by way of limitation the detailed description of the invention is divided into the following subsections:

(i) DDX43 nucleic acids and proteins;
(ii) cancers subject to the invention;
(iii) MEK inhibitors;
(iv) AKT inhibitors;
(v) methods of assessing sensitivity to MEK inhibitors;
(vi) methods of assessing sensitivity to AKT inhibitors;
(vii) methods of measuring mRNA or proteins
(viii) methods of treatment; and
(ix) kits.

"Responder" and "non-responder" are used herein to refer to subjects having cancers that are antagonized by MEK inhibitors, and also are used to refer to the responsive or non-responsive cancers and cancer cells themselves.

5.1 DDX43 Nucleic Acids and Proteins

DDX43 nucleic acids include DNA and RNA comprising at least a portion of a DDX43 gene, a DDX43 mRNA, or a DDX43 cDNA or a sequence complementary or homologous thereto (including but not limited to antisense or small interfering RNA). Said nucleic acid may be comprised of natural nucleotides and may optionally comprise nucleotide bases which are not naturally occurring. In certain non-limiting embodiments, a DDX43 nucleic acid is present in or obtained from a cell of a subject, which may be a cancer cell. In certain other non-limiting embodiments, a DDX43 nucleic acid is a primer or probe which may be used to measure the level of DDX43 expression.

In certain non-limiting embodiments, a DDX43 nucleic acid may be between about 10 and 2707 bases long. In certain non-limiting embodiments, a DDX43 nucleic acid may be at least 10, or at least 15, or at least 20, or at least 30, and up to 30, or up to 50, or up to 100, or up to 200; or between about 10 and 200 or between about 15 and 100 or between about 15 and 50, bases in length.

In certain non-limiting embodiments, a DDX43 nucleic acid may be detectably labeled, for example with a fluorescent, or radioactive, or colorimetric, or affinity label, using methods known in the art.

In a specific non-limiting embodiment, a DDX43 nucleic acid is a human DDX43 nucleic acid molecule which has the nucleic acid sequence as set forth in GenBank/NCBI database accession no. NM_018665 [40-42] or a portion thereof, which portion may be, for example, at least 10, or at least 15, or at least 20, or at least 30, and up to 30, or up to 50, or up to 100, or up to 200; or between about 10 and 200 or between about 15 and 100 or between about 15 and 50, bases in length, or a nucleic acid which is at least about 90 percent or at least about 95 percent or at least about 98 percent homologous to the sequence set forth in NM_018665 or a portion thereof. Homology as referred to herein may be determined using standard software, for example but not limited to BLAST or FASTA.

In other specific non-limiting embodiments, a DDX43 nucleic acid is a cat, chimpanzee, mouse or dog DDX43 nucleic acid molecule which has, respectively, the nucleic acid sequence as set forth in GenBank/NCBI accession nos. XM_003986327.1; XM_518584.3; NM_001191044.1; or XM_848647 [43-46] or a portion thereof, which portion may be, for example, at least 10, or at least 15, or at least 20, or at least 30, or between about 10 and 200 or between about 15 and 100 or between about 15 and 50, bases in length, or a nucleic acid which is at least about 90 percent or at least about 95 percent or at least about 98 percent homologous to the sequence set forth in XM_003986327.1; XM_518584.3; NM_001191044.1; or XM_848647, or a portion thereof.

A DDX43 protein is present in, produced by or obtained from a cell of a subject, which may be a cancer cell. In a specific non-limiting embodiment, a DDX43 protein is a human DDX43 protein molecule which has the amino acid sequence as set forth in GenBank/NCBI database accession no. NM_018665 [40-42] or NP_061135 [47] or a variant thereof which is at least about 90 percent or at least about 95 percent or at least about 98 percent or at least about 99 percent homologous to the sequence set forth in NM_018665 or NP_061135. In other specific non-limiting embodiments, a DDX43 protein is a cat, chimpanzee, mouse or dog DDX43 protein which has, respectively, the amino acid sequence as set forth in GenBank/NCBI accession nos. XM_003986327.1 or XP_003986376 (cat); XM_518584.3 or XP_518584.2 (chimpanzee); NM_001191044.1 or NP_001177973.1 (mouse); or XM_848647 or XP_853740.1 (dog) [43-46, 48-51]

5.2 Cancers Subject to the Invention

In non-limiting embodiments, the invention may be applied to cancers including uveal melanoma, cutaneous melanoma, metastatic melanoma, sarcoma, bladder cancer (e.g. transitional cell carcinoma), breast cancer (e.g., infiltrating ductal carcinoma), astrocytoma, glioblastoma, colon cancer, lung cancer (e.g., lung squamous cell carcinoma), esophageal cancer (e.g. small cell carcinoma), renal cancer (e.g., clear cell carcinoma), liver cancer, small intestine cancer (e.g. papillary adenocarcinoma), and stomach cancer (e.g. adenocarcinoma) [52].

5.3 MEK Inhibitors

The present invention may be used to assess the likelihood of therapeutic benefit to a MEK inhibitor. A MEK inhibitor is an agent which inhibits activity of MEK (Mitogen-activated protein/extracellular signal-regulated kinase kinase. Non-limiting examples of MEK inhibitors include selumetinib, trametinib (GSK1120212; GlaxoSmithKline), MEK162 (Array/Novartis), PD-325901 (Pfizer), XL518 (Exelixis), and CI-1040 (Selleck).

5.4 AKT Inhibitors

According to certain non-limiting embodiments of the invention, if a cancer is resistant to treatment with a MEK inhibitor associated with increased DDX43 expression, it may be susceptible to treatment with an AKT (also known as Protein Kinase B) inhibitor. Non-limiting examples of AKT inhibitors include VQD-002 (VioQuest), perifosine (Selleck), miltefosine (Zentaris), AZD5363 (Astrazeneca) and MK2206 (Merck).

5.5 Methods of Assessing Sensitivity to MEK Inhibitors

A subject may be a human or a non-human subject. Non-limiting examples of non-human subjects include non-human primates, dogs, cats, mice, rats, guinea pigs, rabbits, fowl, pigs, horses, cows, goats, sheep, etc.

Cells for testing may be obtained by any method known in the art, including but not limited to as a surgical resection, as a biopsy for example but not limited to a needle biopsy, core biopsy, or aspirate, or collection from a fluid sample, such as blood, urine, cerebral spinal fluid, cystic fluid, etc.

Methods of measuring mRNA include but are not limited to polymerase chain reaction, in situ hybridization, gel electrophoresis, sequence analysis, and microarray analysis or a combination thereof.

Methods of measuring protein include but are not limited to mass spectrometry techniques, 1-D or 2-D gel-based analysis systems, chromatography, enzyme linked immunosorbent assays (ELISAs), radioimmunoassays (MA), enzyme immunoassays (EIA), Western Blotting, immunoprecipitation, and immunohistochemistry. Antibody arrays or protein chips may also be employed.

That an anticancer effect is "likely" to be produced by an agent in a subject means that the subject, in the parameter or parameters being tested (e.g., level of DDX43 mRNA and/or protein, expression of genes or exons listed in Table 1), is more similar to other subjects in which the agent produces a significant anticancer effect than to other subjects in which the agent does not produce a significant anticancer effect.

That an anticancer effect is "unlikely" to be produced by an agent in a subject means that the subject, in the parameter or parameters being tested, is more similar to other subjects in which the agent does not produce a significant anticancer effect than to other subjects in which the agent does produce a significant anticancer effect.

5.5.1 Using DDX43

In certain embodiments, the present invention provides for measurement of expression of a DDX43 molecule, which may be a measurement of DDX43 mRNA and/or measurement of DDX43 protein. Measurement may be of intracellular levels of mRNA and/or protein. Measurement may be in vitro in a sample, for example a cell sample such as from a biopsy of a cancer (primary or metastatic), from a subject, or may be in vivo using a labeled probe.

In certain non-limiting embodiments, the present invention provides for a method of determining whether an anti-cancer effect is unlikely to be produced in a cancer by a MEK inhibitor, comprising determining whether cells of the cancer contain an increased level of DDX43 mRNA and/or DDX43 protein, where if the level of DDX43 mRNA and/or protein is increased, it is unlikely that a MEK inhibitor would have an anti-cancer effect on the cancer.

In certain non-limiting embodiments, the present invention provides for a method of determining whether an anti-cancer effect is unlikely to be produced in a cancer by a MEK inhibitor, comprising obtaining a sample of the cancer, and determining, in the sample, whether cells of the cancer contain an increased level of DDX43 mRNA and/or DDX43 protein, where if the level of DDX43 mRNA and/or protein is increased, it is unlikely that a MEK inhibitor would have an anti-cancer effect on the cancer.

In certain non-limiting embodiments, the present invention provides for a method of determining whether an anti-cancer effect is unlikely to be produced in a subject having a cancer by a MEK inhibitor, comprising obtaining a sample of the cancer, and determining, in the sample, whether cells of the cancer contain an increased level of DDX43 mRNA and/or DDX43 protein, where if the level of DDX43 mRNA and/or protein is increased, it is unlikely that a MEK inhibitor would have an anti-cancer effect on the cancer.

An increased level of DDX43 mRNA or protein is a significant increase relative to the level of DDX43 mRNA or protein in a normal tissue (a "normal value"). In specific, non-limiting examples, the level of DDX43 mRNA and/or protein may be increased by at least a factor of 10, or at least a factor of 15, or at least a factor of 20, or at least a factor of 30, or at least a factor of 40, or at least a factor of 50, relative to the level in a normal healthy subject or normal tissue in the same subject. In particular non-limiting embodiments the level of DDX43 mRNA and/or protein may be expressed as a ratio relative to the expression of a reference gene, such as a housekeeping gene, which is expected to be expressed at about the same level in normal versus cancer tissue. In non-limiting examples suitable reference genes may be GAPDH, beta-actin or beta-tubulin. In particular non-limiting examples, the ratio of the expression level of DDX43 mRNA or protein, relative to GADPH mRNA or protein (DDX43/GAPDH ratio) or to mRNA or protein expression of another housekeeping gene such as beta actin or beta tubulin, in a responder may be less than 0.5 or less than 0.1 and in a non-responder may be at least 1. In one specific non-limiting example the DDX43/GAPDH ratio in responders may be up to 0.078 and in non-responders may be at least 1.457.

In non-limiting embodiments, a control value may be predetermined or may be determined in parallel or subsequent to an assay determining mRNA and/or protein level in a subject.

An anti-cancer effect means one or more of a reduction in aggregate cancer cell mass, a reduction in cancer cell growth rate, a reduction in cancer cell proliferation, a reduction in tumor mass, a reduction in tumor volume, a reduction in tumor cell proliferation, a reduction in tumor growth rate, or a reduction in tumor metastasis.

In certain non-limiting embodiments, the present invention provides for a method of determining whether an anti-cancer effect is unlikely to be produced in a cancer by selumetinib, comprising determining whether cells of the cancer contain an increased level of DDX43 mRNA and/or DDX43 protein, where if the level of DDX43 mRNA and/or protein is increased, it is unlikely that selumetinib would have an anti-cancer effect on the cancer.

In certain non-limiting embodiments, the present invention provides for a method of determining whether an anti-cancer effect is unlikely to be produced in a cancer by selumetinib, comprising obtaining a sample of the cancer, and determining, in the sample, whether cells of the cancer contain an increased level of DDX43 mRNA and/or DDX43 protein, where if the level of DDX43 mRNA and/or protein is increased, it is unlikely that selumetinib would have an anti-cancer effect on the cancer.

In certain non-limiting embodiments, the present invention provides for a method of determining whether an anti-cancer effect is unlikely to be produced in a subject having a cancer by selumetinib, comprising obtaining a sample of the cancer, and determining, in the sample, whether cells of the cancer contain an increased level of DDX43 mRNA and/or DDX43 protein, where if the level of DDX43 mRNA and/or DDX43 protein is increased, it is unlikely that selumetinib would have an anti-cancer effect on the cancer.

In certain non-limiting embodiments, the present invention provides for a method of determining whether an anti-cancer effect is unlikely to be produced in melanoma by a MEK inhibitor, comprising determining whether cells of the melanoma contain an increased level of DDX43 mRNA and/or DDX43 protein, where if the level of DDX43 mRNA and/or protein is increased, it is unlikely that a MEK inhibitor would have an anti-cancer effect on the melanoma.

In certain non-limiting embodiments, the present invention provides for a method of determining whether an anti-cancer effect is unlikely to be produced in a melanoma by a MEK inhibitor, comprising obtaining a sample of the melanoma, and determining, in the sample, whether cells of the melanoma contain an increased level of DDX43 mRNA and/or DDX43 protein, where if the level of DDX43 mRNA and/or protein is increased, it is unlikely that a MEK inhibitor would have an anti-cancer effect on the melanoma.

In certain non-limiting embodiments, the present invention provides for a method of determining whether an anti-cancer effect is unlikely to be produced in a subject having a melanoma by a MEK inhibitor, comprising obtaining a sample of the melanoma, and determining, in the sample, whether cells of the melanoma contain an increased level of DDX43 mRNA and/or DDX43 protein, where if the level of DDX43 mRNA and/or protein is increased, it is unlikely that a MEK inhibitor would have an anti-cancer effect on the melanoma.

In certain non-limiting embodiments, the present invention provides for a method of determining whether an anti-cancer effect is unlikely to be produced in melanoma by selumetinib, comprising determining whether cells of the melanoma contain an increased level of DDX43 mRNA and/or DDX43 protein, where if the level of DDX43 mRNA and/or protein is increased, it is unlikely that selumetinib would have an anti-cancer effect on the melanoma.

In certain non-limiting embodiments, the present invention provides for a method of determining whether an anti-cancer effect is unlikely to be produced in a melanoma by selumetinib, comprising obtaining a sample of the melanoma, and determining, in the sample, whether cells of the melanoma contain an increased level of DDX43 mRNA and/or DDX43 protein, where if the level of DDX43 mRNA and/or protein is increased, it is unlikely that selumetinib would have an anti-cancer effect on the melanoma.

In certain non-limiting embodiments, the present invention provides for a method of determining whether an anti-cancer effect is unlikely to be produced in a subject having a melanoma by selumetinib, comprising obtaining a sample of the melanoma, and determining, in the sample, whether cells of the melanoma contain an increased level of DDX43 mRNA and/or DDX43 protein, where if the level of DDX43 mRNA and/or protein is increased, it is unlikely that selumetinib would have an anti-cancer effect on the melanoma.

5.5.2 Using Markers Other than DDX43

As demonstrated in the working example below, differential expression levels of other genes (or gene exons) were associated with decreased response to MEK inhibition. In non-limiting embodiments of the invention, differential expression of these genes and/or exons may be used instead of DDX43 or in addition to DDX43 to assess the likelihood that a subject will have a favorable response to treatment.

In certain non-limiting embodiments, the present invention provides for a method of determining whether an anti-cancer effect is unlikely to be produced in a subject cancer by a MEK inhibitor, comprising determining whether cells of the subject cancer contain an increased level, relative to a responder cancer cell, of mRNA and/or protein corresponding to one or more gene or exon listed in Table 1 below, where if the level of mRNA and/or protein is increased, it is unlikely that a MEK inhibitor would have an anti-cancer effect on the subject cancer.

In certain non-limiting embodiments, the present invention provides for a method of determining whether an anti-cancer effect is unlikely to be produced in a subject cancer by a MEK inhibitor, comprising determining whether cells of the subject cancer contain a decreased level, relative to a responder cancer cell, of mRNA and/or protein corresponding to an exon of one or more of the following: RHBG, MFAPS, DPYS, ACCN4, or DMKN, where if the level of mRNA and/or protein is decreased, it is unlikely that a MEK inhibitor would have an anti-cancer effect on the subject cancer.

In certain non-limiting embodiments, the present invention provides for a method of determining whether an anti-cancer effect is unlikely to be produced in a subject cancer by a MEK inhibitor, comprising obtaining a sample of the subject cancer, and determining, in the sample, whether cells of the subject cancer contain an increased level, relative to a responder cancer cell, of mRNA and/or protein corresponding to one or more gene or exon listed in Table 1 below, where if the level of mRNA and/or protein is increased, it is unlikely that a MEK inhibitor would have an anti-cancer effect on the subject cancer.

In certain non-limiting embodiments, the present invention provides for a method of determining whether an anti-cancer effect is unlikely to be produced in a subject cancer by a MEK inhibitor, comprising obtaining a sample of the subject cancer, and determining, in the sample, whether cells of the subject cancer contain a decreased level, relative to a responder cancer cell, of mRNA and/or protein corresponding to an exon of one or more of the following: RHBG, MFAPS, DPYS, ACCN4, or DMKN, where if the level of mRNA and/or protein is decreased, it is unlikely that a MEK inhibitor would have an anti-cancer effect on the subject cancer.

In certain non-limiting embodiments, the present invention provides for a method of determining whether an anti-cancer effect is unlikely to be produced in a subject having a cancer by a MEK inhibitor, comprising obtaining a sample of the subject cancer, and determining, in the sample, whether cells of the subject cancer contain an increased level, relative to a responder cancer cell, of mRNA and/or protein corresponding to one or more gene or exon listed in Table 1 below, where if the level of mRNA and/or protein is increased, it is unlikely that a MEK inhibitor would have an anti-cancer effect on the subject cancer.

In certain non-limiting embodiments, the present invention provides for a method of determining whether an anti-cancer effect is unlikely to be produced in a subject having a cancer by a MEK inhibitor, comprising obtaining a sample of the subject cancer, and determining, in the sample, whether cells of the subject cancer contain a decreased level, relative to a responder cancer cell, of mRNA and/or protein corresponding to an exon of one or more of the following: RHBG, MFAPS, DPYS, ACCN4, or DMKN, where if the level of mRNA and/or protein is increased, it is unlikely that a MEK inhibitor would have an anti-cancer effect on the subject cancer.

TABLE 1

List of genes associated with lack of clinical benefit to selumetinib by differential expression (left) and differential exon levels (right), by comparing "responders" versus "non responders", independently of treatment. p values and log$_2$ fold changes for each gene are also shown.

| Genes Differentially Expressed | | | Exons Differentially Expressed | | |
|---|---|---|---|---|---|
| Gene Symbol | p Value | Log2 FC | Gene Symbol | p Value | Log2 FC |
| RIMS2 | 4.30E−10 | 10.2024 | CAPN3 | 3.33E−16 | 2.8463 |
| DDX43 | 1.67E−08 | 5.8753 | GTF2I | 5.33E−12 | 4.7563 |
| ITLN2 | 2.75E−08 | 6.8585 | XIST | 7.56E−10 | 28.1751 |
| ADAMTS14 | 2.62E−08 | 4.8677 | FMN2 | 9.16E−09 | −4.9091 |
| PCDHGA11 | 1.83E−06 | 4.6135 | RPS24 | 3.62E−07 | −2.2390 |
| FIBCD1 | 3.35E−05 | 3.7236 | | | |
| MRC2 | 0.00011 | 3.4279 | | | |
| SERPINE2 | 0.00013 | 3.4407 | | | |
| DDIT4L | 0.00015 | 3.2857 | | | |
| ICAM5 | 0.00023 | 3.8144 | | | |

In particular, non-limiting embodiments, the one or more gene for which expression is evaluated according to this section is RIMS2, ITLN2, PCHGA11 and/or DDIT4L.

In particular, non-limiting embodiments, the one or more exon for which expression is evaluated according to this section is CAPN3, RHBG, MFAP5, DPYS and/or GTF2I.

5.6 Methods of Assessing Sensitivity to AKT Inhibitors

Cell viability and proliferation rate in response to an AKT inhibitor may optionally be evaluated using standard techniques to determine whether a cell, such as a cancer cell (for example a cancer cell collected from a subject) is sensitive to AKT inhibition.

5.7 Methods of Measuring mRNA or Proteins

In certain non-limiting embodiments, the invention comprises measuring the level of DDX43 mRNA and/or protein, the level of mRNA and/or protein corresponding to one or more gene or exon listed in Table 1, or the level of mRNA and/or protein corresponding to an exon of one or more of the following: RHBG, MFAPS, DPYS, ACCN4, or DMKN. Any methods for measuring the level of mRNA and/or the level of proteins known in the art for can be used for the measurements of the invention. In non-limiting examples, one or more of the following: quantitative real-time PCR, reverse transcriptase PCR, Northern blot, Western blot, immunohistochemistry, and antibody-binding may be used to measure the level of DDX43 mRNA and/or protein, the level of mRNA and/or protein corresponding to one or more gene or exon listed in Table 1, and the level of mRNA and/or protein corresponding to an exon of one or more of the following: RHBG, MFAPS, DPYS, ACCN4, or DMKN.

5.8 Methods of Treatment

In certain non-limiting embodiments, the present invention provides for a method of treating a subject having a cancer comprising (i) determining whether an anti-cancer effect is unlikely to be produced in the cancer by a MEK inhibitor, comprising determining whether cells of the cancer contain an increased level of DDX43 mRNA and/or DDX43 protein; and (ii) treating the subject with a therapeutic amount of a MEK inhibitor if the level of DDX43 mRNA and/or protein is not increased or (iii) treating the subject with a therapeutic amount of an anticancer agent other than a MEK inhibitor where the level of DDX43 mRNA and/or protein is increased. In one specific non-limiting embodiment the anticancer agent other than a MEK inhibitor is an AKT inhibitor.

In certain non-limiting embodiments, the present invention provides for a method of treating a subject having a cancer comprising (i) determining whether an anti-cancer effect is unlikely to be produced in a cancer by a MEK inhibitor, comprising obtaining a sample of the cancer, and determining, in the sample, whether cells of the cancer contain an increased level of DDX43 mRNA and/or DDX43 protein, and (ii) treating the subject with a therapeutic amount of a MEK inhibitor if the level of DDX43 mRNA and/or protein is not increased or (iii) treating the subject with a therapeutic amount of an anticancer agent other than a MEK inhibitor where the level of DDX43 mRNA and/or protein is increased. In one specific non-limiting embodiment the anticancer agent other than a MEK inhibitor is an AKT inhibitor.

In certain non-limiting embodiments, the present invention provides for a method of treating a subject having a cancer comprising (i) determining whether an anti-cancer effect is unlikely to be produced in the subject by a MEK inhibitor, comprising obtaining a sample of the cancer, and determining, in the sample, whether cells of the cancer contain an increased level of DDX43 mRNA and/or DDX43 protein, and (ii) treating the subject with a therapeutic amount of a MEK inhibitor if the level of DDX43 mRNA and/or protein is not increased or (iii) treating the subject with a therapeutic amount of an anticancer agent other than a MEK inhibitor where the level of DDX43 mRNA and/or protein is increased. In one specific non-limiting embodiment the anticancer agent other than a MEK inhibitor is an AKT inhibitor.

In certain non-limiting embodiments, the present invention provides for a method of treating a subject having a cancer comprising (i) determining whether an anti-cancer effect is unlikely to be produced in the cancer by a MEK inhibitor, comprising determining whether cells of the cancer contain an increased level of DDX43 mRNA and/or DDX43 protein and/or an increased level of mRNA or protein corresponding to one or more gene or exon listed in Table 1, and (ii) treating the subject with a therapeutic amount of a MEK inhibitor if the level of DDX43 mRNA and/or protein, and/or the level of mRNA or protein corresponding to one or more gene or exon listed in Table 1, is not increased or (iii) treating the subject with a therapeutic amount of an anticancer agent other than a MEK inhibitor where the level of DDX43 mRNA and/or protein, and/or the level of mRNA or protein corresponding to one or more gene or exon listed in Table 1, is increased. In one specific non-limiting embodiment the anticancer agent other than a MEK inhibitor is an AKT inhibitor.

In certain non-limiting embodiments, the present invention provides for a method of treating a subject having a cancer comprising (i) determining whether an anti-cancer effect is unlikely to be produced in the cancer by a MEK inhibitor, comprising determining whether cells of the cancer contain an increased level of DDX43 mRNA and/or DDX43 protein and/or a decreased level of mRNA or protein corresponding to an exon of one or more of the following: RHBG, MFAPS, DPYS, ACCN4, or DMKN, and (ii) treating the subject with a therapeutic amount of a MEK inhibitor if the level of DDX43 mRNA and/or protein is not increased, and/or the level of mRNA or protein corresponding to an exon of one or more of the following: RHBG, MFAPS, DPYS, ACCN4, or DMKN, is not decreased or (iii) treating the subject with a therapeutic amount of an anti-cancer agent other than a MEK inhibitor where the level of DDX43 mRNA and/or protein is increased, and/or the level of mRNA or protein corresponding to an exon of one or more of the following: RHBG, MFAPS, DPYS, ACCN4, or DMKN, is decreased. In one specific non-limiting embodiment the anticancer agent other than a MEK inhibitor is an AKT inhibitor.

In certain non-limiting embodiments, the present invention provides for a method of treating a subject having a cancer comprising (i) determining whether an anti-cancer effect is unlikely to be produced in the cancer by a MEK inhibitor, comprising obtaining a sample of the cancer, and determining, in the sample, whether cells of the cancer contain an increased level of DDX43 mRNA and/or DDX43 protein and/or an increased level of mRNA or protein corresponding to one or more gene or exon listed in Table 1, and (ii) treating the subject with a therapeutic amount of a MEK inhibitor if the level of DDX43 mRNA and/or protein, and/or the level of mRNA or protein corresponding to one or more of the gene or exon listed in Table 1, is not increased or (iii) treating the subject with a therapeutic amount of an anticancer agent other than a MEK inhibitor where the level of DDX43 mRNA and/or protein, and/or the level of mRNA or protein corresponding to one or more gene or exon listed in Table 1, is increased. In one specific non-limiting embodiment the anticancer agent other than a MEK inhibitor is an AKT inhibitor.

In certain non-limiting embodiments, the present invention provides for a method of treating a subject having a cancer comprising (i) determining whether an anti-cancer effect is unlikely to be produced in the cancer by a MEK inhibitor, comprising obtaining a sample of the cancer, and determining, in the sample, whether cells of the cancer contain an increased level of DDX43 mRNA and/or DDX43 protein and/or a decreased level of mRNA or protein corresponding to an exon of one or more of the following: RHBG, MFAPS, DPYS, ACCN4, or DMKN, and (ii) treating the subject with a therapeutic amount of a MEK inhibitor if the level of DDX43 mRNA and/or protein is not increased, and/or the level of mRNA or protein corresponding to an exon of one or more of the following: RHBG, MFAPS, DPYS, ACCN4, or DMKN, is not decreased or (iii) treating the subject with a therapeutic amount of an anticancer agent other than a MEK inhibitor where the level of DDX43 mRNA and/or protein is increased, and/or the level of mRNA or protein corresponding to an exon of one or more of the following: RHBG, MFAPS, DPYS, ACCN4, or DMKN, is decreased. In one specific non-limiting embodiment the anticancer agent other than a MEK inhibitor is an AKT inhibitor.

In certain non-limiting embodiments, the present invention provides for a method of treating a subject having a cancer comprising (i) determining whether an anti-cancer effect is unlikely to be produced in the subject by a MEK inhibitor, comprising obtaining a sample of the cancer, and determining, in the sample, whether cells of the cancer contain an increased level of DDX43 mRNA and/or DDX43 protein and/or an increased level of mRNA or protein corresponding to one or more gene or exon listed in Table 1, and (ii) treating the subject with a therapeutic amount of a MEK inhibitor if the level of DDX43 mRNA and/or protein, and/or the level of mRNA or protein corresponding to one or more gene or exon listed in Table 1, is not increased or (iii) treating the subject with a therapeutic amount of an anti-cancer agent other than a MEK inhibitor where the level of DDX43 mRNA and/or protein, and/or the level of mRNA or protein corresponding to one or more gene or exon listed in Table 1, is increased. In one specific non-limiting embodiment the anticancer agent other than a MEK inhibitor is an AKT inhibitor.

In certain non-limiting embodiments, the present invention provides for a method of treating a subject having a cancer comprising (i) determining whether an anti-cancer effect is unlikely to be produced in the subject by a MEK inhibitor, comprising obtaining a sample of the cancer, and determining, in the sample, whether cells of the cancer contain an increased level of DDX43 mRNA and/or DDX43 protein and/or a decreased level of mRNA or protein corresponding to an exon of one or more of the following: RHBG, MFAPS, DPYS, ACCN4, or DMKN, and (ii) treating the subject with a therapeutic amount of a MEK inhibitor if the level of DDX43 mRNA and/or protein is not increased and/or the level of mRNA or protein corresponding to an exon of one or more of the following: RHBG, MFAPS, DPYS, ACCN4, or DMKN, is not decreased or (iii) treating the subject with a therapeutic amount of an anticancer agent other than a MEK inhibitor where the level of DDX43 mRNA and/or protein is increased, and/or the level of mRNA or protein corresponding to an exon of one or more of the following: RHBG, MFAPS, DPYS, ACCN4, or DMKN, is decreased. In one specific non-limiting embodiment the anticancer agent other than a MEK inhibitor is an AKT inhibitor.

In certain non-limiting embodiments, the present invention provides for a method of treating a subject having a cancer comprising (i) determining whether an anti-cancer effect is unlikely to be produced in the cancer by selumetinib, comprising determining whether cells of the cancer contain an increased level of DDX43 mRNA and/or DDX43 protein; and (ii) treating the subject with a therapeutic amount of selumetinib if the level of DDX43 mRNA and/or protein is not increased or (iii) treating the subject with a therapeutic amount of an anticancer agent other than a MEK inhibitor where the level of DDX43 mRNA and/or protein is increased. In one specific non-limiting embodiment the anticancer agent other than a MEK inhibitor is an AKT inhibitor.

In certain non-limiting embodiments, the present invention provides for a method of treating a subject having a cancer comprising (i) determining whether an anti-cancer effect is unlikely to be produced in the cancer by selumetinib, comprising obtaining a sample of the cancer, and determining, in the sample, whether cells of the cancer contain an increased level of DDX43 mRNA and/or DDX43 protein, and (ii) treating the subject with a therapeutic amount of selumetinib if the level of DDX43 mRNA and/or protein is not increased or (iii) treating the subject with a therapeutic amount of an anticancer agent other than a MEK inhibitor where the level of DDX43 mRNA and/or protein is increased. In one specific non-limiting embodiment the anticancer agent other than a MEK inhibitor is an AKT inhibitor.

In certain non-limiting embodiments, the present invention provides for a method of treating a subject having a cancer comprising (i) determining whether an anti-cancer effect is unlikely to be produced in the subject by selumetinib, comprising obtaining a sample of the cancer, and determining, in the sample, whether cells of the cancer contain an increased level of DDX43 mRNA and/or DDX43 protein, and (ii) treating the subject with a therapeutic amount of selumetinib if the level of DDX43 mRNA and/or protein is not increased or (iii) treating the subject with a therapeutic amount of an anticancer agent other than a MEK inhibitor where the level of DDX43 mRNA and/or protein is increased. In one specific non-limiting embodiment the anticancer agent other than a MEK inhibitor is an AKT inhibitor.

In certain non-limiting embodiments, the present invention provides for a method of treating a subject having a cancer comprising (i) determining whether an anti-cancer effect is unlikely to be produced in the cancer by selumetinib, comprising determining whether cells of the cancer contain an increased level of DDX43 mRNA and/or DDX43 protein and/or an increased level of mRNA or protein corresponding to one or more gene or exon listed in Table 1, and (ii) treating the subject with a therapeutic amount of selumetinib if the level of DDX43 mRNA and/or protein, and/or the level of mRNA or protein corresponding to one or more gene or exon listed in Table 1, is not increased or (iii) treating the subject with a therapeutic amount of an anticancer agent other than a MEK inhibitor where the level of DDX43 mRNA and/or protein, and/or the level of mRNA or protein corresponding to one or more gene or exon listed in Table 1, is increased. In one specific non-limiting embodiment the anticancer agent other than a MEK inhibitor is an AKT inhibitor.

In certain non-limiting embodiments, the present invention provides for a method of treating a subject having a cancer comprising (i) determining whether an anti-cancer effect is unlikely to be produced in the cancer by selumetinib, comprising determining whether cells of the cancer contain an increased level of DDX43 mRNA and/or DDX43 protein and/or a decreased level of mRNA or protein corresponding to an exon of one or more of the following: RHBG, MFAPS, DPYS, ACCN4, or DMKN, and (ii) treating the subject with a therapeutic amount of selumetinib if the level of DDX43 mRNA and/or protein is not increased, and/or the level of mRNA or protein corresponding to an exon of one or more of the following: RHBG, MFAPS, DPYS, ACCN4, or DMKN, is not decreased or (iii) treating the subject with a therapeutic amount of an anticancer agent other than a MEK inhibitor where the level of DDX43 mRNA and/or protein is increased, and/or the level of mRNA or protein corresponding to an exon of one or more of the following: RHBG, MFAPS, DPYS, ACCN4, or DMKN, is decreased. In one specific non-limiting embodiment the anticancer agent other than a MEK inhibitor is an AKT inhibitor.

In certain non-limiting embodiments, the present invention provides for a method of treating a subject having a cancer comprising (i) determining whether an anti-cancer effect is unlikely to be produced in the cancer by selumetinib, comprising obtaining a sample of the cancer, and determining, in the sample, whether cells of the cancer contain an increased level of DDX43 mRNA and/or DDX43 protein and/or an increased level of mRNA or protein corresponding to one or more gene or exon listed in Table 1, and (ii) treating the subject with a therapeutic amount of selumetinib if the level of DDX43 mRNA and/or protein, and/or the level of mRNA or protein corresponding to one or more gene or exon listed in Table 1, is not increased or (iii) treating the subject with a therapeutic amount of an anticancer agent other than a MEK inhibitor where the level of DDX43 mRNA and/or protein, and/or the level of mRNA or protein corresponding to one or more gene or exon listed in Table 1, is increased. In one specific non-limiting embodiment the anticancer agent other than a MEK inhibitor is an AKT inhibitor.

In certain non-limiting embodiments, the present invention provides for a method of treating a subject having a cancer comprising (i) determining whether an anti-cancer effect is unlikely to be produced in the cancer by selumetinib, comprising obtaining a sample of the cancer, and determining, in the sample, whether cells of the cancer contain an increased level of DDX43 mRNA and/or DDX43 protein and/or a decreased level of mRNA or protein corresponding to an exon of one or more of the following: RHBG, MFAPS, DPYS, ACCN4, or DMKN, and (ii) treating the subject with a therapeutic amount of selumetinib if the level of DDX43 mRNA and/or protein is not increased, and/or the level of mRNA or protein corresponding to an exon of one or more of the following: RHBG, MFAPS, DPYS, ACCN4, or DMKN, is not decreased or (iii) treating the subject with a therapeutic amount of an anticancer agent other than a MEK inhibitor where the level of DDX43 mRNA and/or protein is increased, and/or the level of mRNA or protein corresponding to an exon of one or more of the following: RHBG, MFAPS, DPYS, ACCN4, or DMKN, is decreased. In one specific non-limiting embodiment the anticancer agent other than a MEK inhibitor is an AKT inhibitor.

In certain non-limiting embodiments, the present invention provides for a method of treating a subject having a cancer comprising (i) determining whether an anti-cancer effect is unlikely to be produced in the subject by selumetinib, comprising obtaining a sample of the cancer, and determining, in the sample, whether cells of the cancer contain an increased level of DDX43 mRNA and/or DDX43 protein and/or an increased level of mRNA or protein corresponding to one or more of the gene or exon listed in Table 1, and (ii) treating the subject with a therapeutic amount of selumetinib if the level of DDX43 mRNA and/or protein, and/or the level of mRNA or protein corresponding to one or more gene or exon listed in Table 1, is not increased or (iii) treating the subject with a therapeutic amount of an anticancer agent other than a MEK inhibitor where the level of DDX43 mRNA and/or protein, and/or the level of mRNA or protein corresponding to one or more gene or exon listed in Table 1, is increased. In one specific non-limiting embodiment the anticancer agent other than a MEK inhibitor is an AKT inhibitor.

In certain non-limiting embodiments, the present invention provides for a method of treating a subject having a cancer comprising (i) determining whether an anti-cancer effect is unlikely to be produced in the subject by selumetinib, comprising obtaining a sample of the cancer, and determining, in the sample, whether cells of the cancer contain an increased level of DDX43 mRNA and/or DDX43 protein and/or a decreased level of mRNA or protein corresponding to an exon of one or more of the following: RHBG, MFAPS, DPYS, ACCN4, or DMKN, and (ii) treating the subject with a therapeutic amount of selumetinib if the level of DDX43 mRNA and/or protein is not increased, and/or the level of mRNA or protein corresponding to an exon of one or more of the following: RHBG, MFAPS, DPYS, ACCN4, or DMKN, is not decreased or (iii) treating the subject with a therapeutic amount of an anticancer agent other than a MEK inhibitor where the level of DDX43 mRNA and/or protein is increased, and/or the level of mRNA or protein corresponding to an exon of one or more of the following: RHBG, MFAPS, DPYS, ACCN4, or DMKN, is decreased. In one specific non-limiting embodiment the anticancer agent other than a MEK inhibitor is an AKT inhibitor.

In certain non-limiting embodiments, the present invention provides for a method of treating a subject having a melanoma comprising (i) determining whether an anti-cancer effect is unlikely to be produced in the melanoma by a MEK inhibitor, comprising determining whether cells of the melanoma contain an increased level of DDX43 mRNA and/or DDX43 protein; and (ii) treating the subject with a therapeutic amount of a MEK inhibitor if the level of DDX43 mRNA and/or protein is not increased or (iii) treating the subject with a therapeutic amount of an anticancer agent other than a MEK inhibitor where the level of DDX43 mRNA and/or protein is increased. In one specific non-limiting embodiment the anticancer agent other than a MEK inhibitor is an AKT inhibitor.

In certain non-limiting embodiments, the present invention provides for a method of treating a subject having a melanoma comprising (i) determining whether an anti-cancer effect is unlikely to be produced in the melanoma by a MEK inhibitor, comprising obtaining a sample of the melanoma, and determining, in the sample, whether cells of the melanoma contain an increased level of DDX43 mRNA and/or DDX43 protein, and (ii) treating the subject with a therapeutic amount of a MEK inhibitor if the level of DDX43 mRNA and/or protein is not increased or (iii) treating the subject with a therapeutic amount of an anticancer agent other than a MEK inhibitor where the level of DDX43 mRNA and/or protein is increased. In one specific non-limiting embodiment the anticancer agent other than a MEK inhibitor is an AKT inhibitor.

In certain non-limiting embodiments, the present invention provides for a method of treating a subject having a melanoma comprising (i) determining whether an anti-cancer effect is unlikely to be produced in the subject by a MEK inhibitor, comprising obtaining a sample of the melanoma, and determining, in the sample, whether cells of the melanoma contain an increased level of DDX43 mRNA and/or DDX43 protein, and (ii) treating the subject with a therapeutic amount of a MEK inhibitor if the level of DDX43 mRNA and/or protein is not increased or (iii) treating the subject with a therapeutic amount of an anticancer agent other than a MEK inhibitor where the level of DDX43 mRNA and/or protein is increased. In one specific non-limiting embodiment the anticancer agent other than a MEK inhibitor is an AKT inhibitor.

In certain non-limiting embodiments, the present invention provides for a method of treating a subject having a melanoma comprising (i) determining whether an anti-cancer effect is unlikely to be produced in the melanoma by a MEK inhibitor, comprising determining whether cells of the melanoma contain an increased level of DDX43 mRNA and/or DDX43 protein and/or an increased level of mRNA or protein corresponding to one or more gene or exon listed in Table 1, and (ii) treating the subject with a therapeutic amount of a MEK inhibitor if the level of DDX43 mRNA and/or protein, and/or the level of mRNA or protein corresponding to one or more gene or exon listed in Table 1, is not increased or (iii) treating the subject with a therapeutic amount of an anticancer agent other than a MEK inhibitor where the level of DDX43 mRNA and/or protein, and/or the level of mRNA or protein corresponding to one or more gene or exon listed in Table 1, is increased. In one specific non-limiting embodiment the anticancer agent other than a MEK inhibitor is an AKT inhibitor.

In certain non-limiting embodiments, the present invention provides for a method of treating a subject having a melanoma comprising (i) determining whether an anti-cancer effect is unlikely to be produced in the melanoma by a MEK inhibitor, comprising determining whether cells of the melanoma contain an increased level of DDX43 mRNA and/or DDX43 protein and/or a decreased level of mRNA or protein corresponding to an exon of one or more of the following: RHBG, MFAPS, DPYS, ACCN4, or DMKN, and (ii) treating the subject with a therapeutic amount of a MEK inhibitor if the level of DDX43 mRNA and/or protein is not increased, and/or the level of mRNA or protein corresponding to an exon of one or more of the following: RHBG, MFAPS, DPYS, ACCN4, or DMKN, is not decreased or (iii) treating the subject with a therapeutic amount of an anticancer agent other than a MEK inhibitor where the level of DDX43 mRNA and/or protein is increased, and/or the level of mRNA or protein corresponding to an exon of one or more of the following: RHBG, MFAPS, DPYS, ACCN4, or DMKN, is decreased. In one specific non-limiting embodiment the anticancer agent other than a MEK inhibitor is an AKT inhibitor.

In certain non-limiting embodiments, the present invention provides for a method of treating a subject having a melanoma comprising (i) determining whether an anticancer effect is unlikely to be produced in the melanoma by a MEK inhibitor, comprising obtaining a sample of the melanoma, and determining, in the sample, whether cells of the melanoma contain an increased level of DDX43 mRNA and/or DDX43 protein and/or an increased level of mRNA or protein corresponding to one or more gene or exon listed in Table 1, and (ii) treating the subject with a therapeutic amount of a MEK inhibitor if the level of DDX43 mRNA and/or protein, and/or the level of mRNA or protein corresponding to one or more gene or exon listed in Table 1, is not increased or (iii) treating the subject with a therapeutic amount of an anticancer agent other than a MEK inhibitor where the level of DDX43 mRNA and/or protein, and/or the level of mRNA or protein corresponding to one or more gene or exon listed in Table 1, is increased. In one specific non-limiting embodiment the anticancer agent other than a MEK inhibitor is an AKT inhibitor.

In certain non-limiting embodiments, the present invention provides for a method of treating a subject having a melanoma comprising (i) determining whether an anticancer effect is unlikely to be produced in the melanoma by a MEK inhibitor, comprising obtaining a sample of the melanoma, and determining, in the sample, whether cells of the melanoma contain an increased level of DDX43 mRNA and/or DDX43 protein and/or a decreased level of mRNA or protein corresponding to an exon of one or more of the following: RHBG, MFAPS, DPYS, ACCN4, or DMKN, and (ii) treating the subject with a therapeutic amount of a MEK inhibitor if the level of DDX43 mRNA and/or protein is not increased, and/or the level of mRNA or protein corresponding to an exon of one or more of the following: RHBG, MFAPS, DPYS, ACCN4, or DMKN, is not decreased or (iii) treating the subject with a therapeutic amount of an anticancer agent other than a MEK inhibitor where the level of DDX43 mRNA and/or protein is increased, and/or the level of mRNA or protein corresponding to an exon of one or more of the following: RHBG, MFAPS, DPYS, ACCN4, or DMKN, is decreased. In one specific non-limiting embodiment the anticancer agent other than a MEK inhibitor is an AKT inhibitor.

In certain non-limiting embodiments, the present invention provides for a method of treating a subject having a melanoma comprising (i) determining whether an anticancer effect is unlikely to be produced in the subject by a MEK inhibitor, comprising obtaining a sample of the melanoma, and determining, in the sample, whether cells of the melanoma contain an increased level of DDX43 mRNA and/or DDX43 protein and/or an increased level of mRNA or protein corresponding to one or more gene or exon listed in Table 1, and (ii) treating the subject with a therapeutic amount of a MEK inhibitor if the level of DDX43 mRNA and/or protein, and/or the level of mRNA or protein corresponding to one or more gene or exon listed in Table 1, is not increased or (iii) treating the subject with a therapeutic amount of an anticancer agent other than a MEK inhibitor where the level of DDX43 mRNA and/or protein, and/or the level of mRNA or protein corresponding to one or more gene or exon listed in Table 1, is increased. In one specific non-limiting embodiment the anticancer agent other than a MEK inhibitor is an AKT inhibitor.

In certain non-limiting embodiments, the present invention provides for a method of treating a subject having a melanoma comprising (i) determining whether an anticancer effect is unlikely to be produced in the subject by a MEK inhibitor, comprising obtaining a sample of the melanoma, and determining, in the sample, whether cells of the melanoma contain an increased level of DDX43 mRNA and/or DDX43 protein and/or a decreased level of mRNA or protein corresponding to an exon of one or more of the following: RHBG, MFAPS, DPYS, ACCN4, or DMKN, and (ii) treating the subject with a therapeutic amount of a MEK inhibitor if the level of DDX43 mRNA and/or protein is not increased, and/or the level of mRNA or protein corresponding to an exon of one or more of the following: RHBG, MFAPS, DPYS, ACCN4, or DMKN, is not decreased or (iii) treating the subject with a therapeutic amount of an anticancer agent other than a MEK inhibitor where the level of DDX43 mRNA and/or protein is increased, and/or the level of mRNA or protein corresponding to an exon of one or more of the following: RHBG, MFAPS, DPYS, ACCN4, or DMKN, is decreased. In one specific non-limiting embodiment the anticancer agent other than a MEK inhibitor is an AKT inhibitor.

In certain non-limiting embodiments, the present invention provides for a method of treating a subject having a melanoma comprising (i) determining whether an anticancer effect is unlikely to be produced in the cancer by selumetinib, comprising determining whether cells of the melanoma contain an increased level of DDX43 mRNA and/or DDX43 protein; and (ii) treating the subject with a therapeutic amount of selumetinib if the level of DDX43 mRNA and/or protein is not increased or (iii) treating the subject with a therapeutic amount of an anticancer agent other than a MEK inhibitor where the level of DDX43 mRNA and/or protein is increased. In one specific non-limiting embodiment the anticancer agent other than a MEK inhibitor is an AKT inhibitor.

In certain non-limiting embodiments, the present invention provides for a method of treating a subject having a melanoma comprising (i) determining whether an anticancer effect is unlikely to be produced in the melanoma by selumetinib, comprising obtaining a sample of the melanoma, and determining, in the sample, whether cells of the melanoma contain an increased level of DDX43 mRNA and/or DDX43 protein, and (ii) treating the subject with a therapeutic amount of selumetinib if the level of DDX43 mRNA and/or protein is not increased or (iii) treating the subject with a therapeutic amount of an anticancer agent other than a MEK inhibitor where the level of DDX43 mRNA and/or protein is increased. In one specific non-limiting embodiment the anticancer agent other than a MEK inhibitor is an AKT inhibitor.

In certain non-limiting embodiments, the present invention provides for a method of treating a subject having a melanoma comprising (i) determining whether an anticancer effect is unlikely to be produced in the subject by selumetinib, comprising obtaining a sample of the melanoma, and determining, in the sample, whether cells of the melanoma contain an increased level of DDX43 mRNA and/or DDX43 protein, and (ii) treating the subject with a therapeutic amount of selumetinib if the level of DDX43 mRNA and/or protein is not increased or (iii) treating the subject with a therapeutic amount of an anticancer agent other than a MEK inhibitor where the level of DDX43 mRNA and/or protein is increased. In one specific non-limiting embodiment the anticancer agent other than a MEK inhibitor is an AKT inhibitor.

In certain non-limiting embodiments, the present invention provides for a method of treating a subject having a melanoma comprising (i) determining whether an anticancer effect is unlikely to be produced in the melanoma by selumetinib, comprising determining whether cells of the melanoma contain an increased level of DDX43 mRNA and/or DDX43 protein and/or an increased level of mRNA or protein corresponding to one or more gene or exon listed in Table 1, and (ii) treating the subject with a therapeutic amount of selumetinib if the level of DDX43 mRNA and/or protein, and/or the level of mRNA or protein corresponding to one or more gene or exon listed in Table 1, is not increased or (iii) treating the subject with a therapeutic amount of an anticancer agent other than a MEK inhibitor where the level of DDX43 mRNA and/or protein, and/or the level of mRNA or protein corresponding to one or more gene or exon listed in Table 1, is increased. In one specific non-limiting embodiment the anticancer agent other than a MEK inhibitor is an AKT inhibitor.

In certain non-limiting embodiments, the present invention provides for a method of treating a subject having a melanoma comprising (i) determining whether an anticancer effect is unlikely to be produced in the melanoma by selumetinib, comprising determining whether cells of the melanoma contain an increased level of DDX43 mRNA and/or DDX43 protein and/or a decreased level of mRNA or protein corresponding to an exon of one or more of the following: RHBG, MFAPS, DPYS, ACCN4, or DMKN, and (ii) treating the subject with a therapeutic amount of selumetinib if the level of DDX43 mRNA and/or protein is not increased, and/or the level of mRNA or protein corresponding to an exon of one or more of the following: RHBG, MFAPS, DPYS, ACCN4, or DMKN, is not decreased or (iii) treating the subject with a therapeutic amount of an anticancer agent other than a MEK inhibitor where the level of DDX43 mRNA and/or protein is increased, and/or the level of mRNA or protein corresponding to an exon of one or more of the following: RHBG, MFAPS, DPYS, ACCN4, or DMKN, is decreased. In one specific non-limiting embodiment the anticancer agent other than a MEK inhibitor is an AKT inhibitor.

In certain non-limiting embodiments, the present invention provides for a method of treating a subject having a melanoma comprising (i) determining whether an anticancer effect is unlikely to be produced in the melanoma by selumetinib, comprising obtaining a sample of the melanoma, and determining, in the sample, whether cells of the melanoma contain an increased level of DDX43 mRNA and/or DDX43 protein and/or an increased level of mRNA or protein corresponding to one or more gene or exon listed in Table 1, and (ii) treating the subject with a therapeutic amount of selumetinib if the level of DDX43 mRNA and/or protein, and/or the level of mRNA or protein corresponding to one or more gene or exon listed in Table 1, is not increased or (iii) treating the subject with a therapeutic amount of an anticancer agent other than a MEK inhibitor where the level of DDX43 mRNA and/or protein, and/or the level of mRNA or protein corresponding to one or more gene or exon listed in Table 1, is increased. In one specific non-limiting embodiment the anticancer agent other than a MEK inhibitor is an AKT inhibitor.

In certain non-limiting embodiments, the present invention provides for a method of treating a subject having a melanoma comprising (i) determining whether an anticancer effect is unlikely to be produced in the melanoma by selumetinib, comprising obtaining a sample of the melanoma, and determining, in the sample, whether cells of the melanoma contain an increased level of DDX43 mRNA and/or DDX43 protein and/or a decreased level of mRNA or protein corresponding to an exon of one or more of the following: RHBG, MFAPS, DPYS, ACCN4, or DMKN, and (ii) treating the subject with a therapeutic amount of selumetinib if the level of DDX43 mRNA and/or protein is not increased, and/or the level of mRNA or protein corresponding to an exon of one or more of the following: RHBG, MFAPS, DPYS, ACCN4, or DMKN, is not decreased or (iii) treating the subject with a therapeutic amount of an anticancer agent other than a MEK inhibitor where the level of DDX43 mRNA and/or protein is increased, and/or the level of mRNA or protein corresponding to an exon of one or more of the following: RHBG, MFAPS, DPYS, ACCN4, or DMKN, is decreased. In one specific non-limiting embodiment the anticancer agent other than a MEK inhibitor is an AKT inhibitor.

In certain non-limiting embodiments, the present invention provides for a method of treating a subject having a melanoma comprising (i) determining whether an anticancer effect is likely to be produced in the subject by selumetinib, comprising obtaining a sample of the melanoma, and determining, in the sample, whether cells of the melanoma contain an increased level of DDX43 mRNA and/or DDX43 protein and/or an increased level of mRNA or protein corresponding to one or more gene or exon listed in Table 1, and (ii) treating the subject with a therapeutic amount of selumetinib if the level of DDX43 mRNA and/or protein, and/or the level of mRNA or protein corresponding to one or more gene or exon listed in Table 1, is not increased or (iii) treating the subject with a therapeutic amount of an anticancer agent other than a MEK inhibitor where the level of DDX43 mRNA and/or protein, and/or the level of mRNA or protein corresponding to one or more gene or exon listed in Table 1, is increased. In one specific non-limiting embodiment the anticancer agent other than a MEK inhibitor is an AKT inhibitor.

In certain non-limiting embodiments, the present invention provides for a method of treating a subject having a melanoma comprising (i) determining whether an anticancer effect is likely to be produced in the subject by selumetinib, comprising obtaining a sample of the melanoma, and determining, in the sample, whether cells of the melanoma contain an increased level of DDX43 mRNA and/or DDX43 protein and/or a decreased level of mRNA or protein corresponding to an exon of one or more of the following: RHBG, MFAPS, DPYS, ACCN4, or DMKN, and (ii) treating the subject with a therapeutic amount of selumetinib if the level of DDX43 mRNA and/or protein is not increased, and/or the level of mRNA or protein corresponding to an exon of one or more of the following: RHBG, MFAPS, DPYS, ACCN4, or DMKN, is not decreased or (iii) treating the subject with a therapeutic amount of an anticancer agent other than a MEK inhibitor where the level of DDX43 mRNA and/or protein is increased, and/or the level of mRNA or protein corresponding to an exon of one or more of the following: RHBG, MFAPS, DPYS, ACCN4, or DMKN, is decreased. In one specific non-limiting embodiment the anticancer agent other than a MEK inhibitor is an AKT inhibitor.

A therapeutically effective amount is an amount that is able to achieve one or more of an anticancer effect, prolongation of survival, and/or prolongation of period until relapse.

In certain non-limiting embodiments, a therapeutically effective amount of selumetinib is between 50 mg and 200 mg/day, for example, 50 mg taken orally twice a day or 75 mg taken orally twice a day.

5.9 Kits

In non-limiting embodiments, the present invention provides for a kit for determining whether an anti-cancer effect is unlikely to be produced in a cancer by a MEK inhibitor, comprising a means for determining the level of DDX43 mRNA and/or protein in a cell or cells of the cancer.

In other non-limiting embodiments, the present invention provides for a kit for determining whether an anti-cancer effect is unlikely to be produced in a cancer by a MEK inhibitor, comprising a means for determining the level of mRNA and/or protein corresponding to one or more gene or exon listed in Table 1 or an exon of one or more of the following: RHBG, MFAPS, DPYS, ACCN4, or DMKN, including but not limited to RIMS2, ITLN2, PCHGA11, DDIT4L, CAPN3, RHBG, MFAP5, DPYS and/or GTF2I (these, and DDX43, referred to as "biomarkers").

Types of kits include, but are not limited to, packaged probe and primer sets (e.g. TaqMan probe/primer sets), arrays/microarrays, biomarker-specific antibodies and beads, which further contain one or more probes, primers, or other detection reagents for detecting one or more biomarkers of the present invention.

In a specific, non-limiting embodiment, a kit may comprise a pair of oligonucleotide primers, suitable for polymerase chain reaction (PCR) or nucleic acid sequencing, for measuring levels of mRNA. A pair of primers may comprise nucleotide sequences complementary to a biomarker set forth above, and be of sufficient length to selectively hybridize with said biomarker. Alternatively, the complementary nucleotides may selectively hybridize to a specific region in close enough proximity 5' and/or 3' to the biomarker position to perform PCR and/or sequencing. Multiple biomarker-specific primers may be included in the kit. The kit may also comprise one or more polymerases, reverse transcriptase, and nucleotide bases, wherein the nucleotide bases can be further detectably labeled.

In non-limiting embodiments, a primer may be at least about 10 nucleotides or at least about 15 nucleotides or at least about 20 nucleotides in length and/or up to about 200 nucleotides or up to about 150 nucleotides or up to about 100 nucleotides or up to about 75 nucleotides or up to about 50 nucleotides in length.

In a further non-limiting embodiment, the oligonucleotide primers may be immobilized on a solid surface or support, for example, on a nucleic acid microarray, wherein the position of each oligonucleotide primer bound to the solid surface or support is known and identifiable.

In a specific, non-limiting embodiment, a kit may comprise at least one nucleic acid probe, suitable for in situ hybridization or fluorescent in situ hybridization, for measuring mRNA. Such kits will generally comprise one or more oligonucleotide probes that have specificity for various biomarkers.

In other non-limiting embodiments, a kit may comprise at least one antibody for immunodetection of the biomarker(s). Antibodies, both polyclonal and monoclonal, specific for a biomarker, may be prepared using conventional immunization techniques, as will be generally known to those of skill in the art. The immunodetection reagents of the kit may include detectable labels that are associated with, or linked to, the given antibody or antigen itself. Such detectable labels include, for example, chemiluminescent or fluorescent molecules (rhodamine, fluorescein, green fluorescent protein, luciferase, Cy3, Cy5, or ROX), radiolabels (3H, 35S, 32P, 14C, 131I) or enzymes (alkaline phosphatase, horseradish peroxidase).

In a further non-limiting embodiment, the biomarker-specific antibody may be provided bound to a solid support, such as a column matrix, an array, or well of a microtiter plate. Alternatively, the support may be provided as a separate element of the kit.

In certain non-limiting embodiments, where the measurement means in the kit employs an array, the set of biomarkers set forth above may constitute at least 10 percent or at least 20 percent or at least 30 percent or at least 40 percent or at least 50 percent or at least 60 percent or at least 70 percent or at least 80 percent of the species of markers represented on the microarray.

In certain non-limiting embodiments, a kit may comprise one or more detection reagents and other components (e.g. a buffer, enzymes such as DNA polymerases or ligases, chain extension nucleotides such as deoxynucleotide triphosphates, and in the case of Sanger-type DNA sequencing reactions, chain terminating nucleotides, positive control sequences, negative control sequences, and the like) necessary to carry out an assay or reaction to detect a biomarker.

In certain non-limiting embodiments, a kit may comprise a normal control sample or may disclose, in a written material, a normal control value.

A kit may further contain means for comparing the biomarker with a standard, and can include instructions for using the kit to detect the biomarker of interest. Specifically, the instructions indicate that an increased level, in a cancer cell or cells, of mRNA or protein corresponding to DDX43, or another biomarker listed in Table 1, or a decreased level of mRNA or protein corresponding to an exon of one or more of the following: RHBG, MFAPS, DPYS, ACCN4, or DMKN, indicates that it is unlikely that a MEK inhibitor such as selumetinib would have an anti-cancer effect on the cancer. In certain non-limiting embodiments the invention provides for a kit for determining whether an anti-cancer effect is likely to be produced in a cancer by a MEK inhibitor, comprising a means for determining the level of DDX43 mRNA and/or protein in a cell or cells of the cancer together with a disclosure that an increased level of DDX43 expression in a cancer is associated with a lower likelihood that a MEK inhibitor will have an anticancer effect against the cancer. In certain non-limiting embodiments the invention provides for a kit for determining whether an anti-cancer effect is likely to be produced in a cancer by a MEK inhibitor, comprising a means for determining the level of mRNA or protein corresponding to one or more gene or exon listed in Table 1 together with a disclosure that an increased level of said gene(s) and/or exon(s) in a cancer is associated with a lower likelihood that a MEK inhibitor will have an anticancer effect against the cancer. In certain non-limiting embodiments the invention provides for a kit for determining whether an anti-cancer effect is likely to be produced in a cancer by a MEK inhibitor, comprising a means for determining the level of mRNA or protein corresponding to an exon of one or more of the following: RHBG, MFAP5, DPYS, ACCN4, or DMKN, together with a disclosure that an decreased level of exon(s) in a cancer is associated with a lower likelihood that a MEK inhibitor will have an anticancer effect against the cancer.

6. EXAMPLE: DDX43 MEDIATES RESISTANCE TO MEK1/2 BY REGULATING RAS EXPRESSION IN GNAQ MUTANT UVEAL MELANOMA

6.1 Materials and Methods

Whole-Transcriptome Sequencing. Matched tumor biopsies were collected from patients with metastatic uveal melanoma carrying GNA11 or GNAQ mutations (clinicaltrials.gov # NCT01143402), before and after 14 days of selumetinib treatment. Total RNA was extracted from flash frozen specimens using Trizol (Invitrogen) followed by DNase digestion and Qiagen RNeasy (Qiagen, Valencia, Calif.) column purification following the manufacture's protocol. The RNA integrity was verified using an Agilent Bioanalyzer 2100 (Agilent). RNA was processed using an Illumina RNA-seq sample prep kit following the manufacturer's instructions (Illumina, San Diego, Calif.).

RNA-Seq on Applied Biosystem SOLiD.

Taqman gene expression assay primers and probes for DDX43 and glyceraldehyde 3-phosphate dehydrogenase (GAPDH) were purchased from Applied Biosystems, and real-time PCR assays were performed using Applied Biosystem 7500.

Data Analysis and Bio-Informatics.

RNA-seq reads were aligned using the Tophat2 tool [39]. The reads were further assigned to the exonic regions of each gene by running htseq.py [25]. Counts data was normalized using default DESeq normalization and clustered using hierarchical clustering with Euclidian distance measure on log 2 counts. Differential analysis of genes was performed using DESeq R package [25]. Genes that have at least 2 fold change and False Discovery Rate (FDR) of 0.05 were flagged as significant.

Quantitative Real-Time PCR.

RNA was extracted with Trizol Reagent (Invitrogen). The quality of RNA was checked with the RNA 6000 NanoAssay and a Bioanalyzer 2100 (Agilent). 1 µg of total RNA was reverse-transcribed using the Thermoscript RT-PCR system (Life Technologies). The resultant cDNA was used in a RT-PCR reactions using an iCycler (Bio-Rad) and pre-designed TaqMan Gene expression Assays for DDX43 and glyceraldehyde-3-phosphate dehydrogenase (GAPDH) genes (Life Technologies). Triplicates CT values were averaged, amounts of target were interpolated from the standard curves and normalized to GAPDH.

Cell Culture.

Omm1.3 and Mel270 (Dr Bruce Ksander). UM cell lines have been sequenced for the presence of activating mutations in codons 209 (exon 5) and 183 (exon 4) of GNAQ and GNA11. Cells were cultured in RPMI medium supplemented with 10% fetal bovine serum, 100 units/ml penicillin and 100 µg/ml streptomycin, and maintained at 37° C. in 5% CO2. Cells were treated with selumetinib (AZD6244, ARRY-142866, AstraZeneca) and MK2206 (Merck).

Cell Viability Assays.

Cells were plated in 96-well plates, and treated with the indicated concentrations of drugs. Viability was assessed after five days of treatment using the Cell Counting Kit 8 (CCK8) from Dojindo Molecular Technologies (Gaithersburg, Md.) according to the manufacturer's instructions. Cell viability is expressed as a percentage of untreated cells.

Immunoblotting.

Biopsy tissues or cells were lysed in RIPA buffer supplemented with protease inhibitor cocktail tablets (Roche Diagnostics) and 1 mM NaVO$_3$. Total protein concentration of the lysates was measured by Bio-Rad protein assay (Bio-Rad), and equal amounts of protein were loaded on 4-12% PAGE gels (Invitrogen). PVDF membranes were blocked with 5% nonfat dried milk in PBS buffer containing 0.1% Tween-20 (PBST) for 1 hour and probed with antibody for pERK, ERK, pAKT, pan-AKT, c-Jun, cyclin D1, tubulin (Cell Signaling), DDX43 (Abcam), KRAS, HRAS (Abnova) and NRAS (Santa Cruz Biotechnology).

RNAi-Mediated Gene Knockdown.

Small interfering RNA against GNAQ (sc-35429), DDX43, KRAS (sc-35731), NRAS (sc-36004), HRAS (sc-29340) and control siRNA (sc-37007) were purchased from Santa Cruz Biotechnology. DDX43-1 and -2 siRNA were from OriGene. They were transfected using Lipofectamine RNAiMAX reagent (Invitrogen) following the manufacturer's instructions. The human DDX43 cDNA clone in pCMV6-XL5 (or PCMV6-Neo) was from OriGene.

6.2 Results

Differential Expression of Genes in Liver Biopsies of Patients with Uveal Melanoma.

It has been reported that selumetinib inhibits pERK and induces cell cycle arrest in UM cells with GNAQ mutations [7]. Selumetinib is currently in Phase II clinical trial for patients with metastatic uveal melanoma [8]. In order to identify potential markers of drug resistance, whole-transcriptome sequencing technology (RNA seq) was performed on liver metastases of patients with uveal melanoma carrying GNAQ or GNA11 mutations.

Transcription expression profiles of biopsies from patients who had partial response or stable disease were compared with the profiles of patients with progressive disease. The analysis of differentially expressed genes was performed using DESeq R package [25]. Genes that had at least log 2 fold change >2 and False Discovery Rate (FDR) of 0.05 were flagged as significant. Several genes, including RIMS2, DDX43, ITLN2, PCHGA11, and DDIT4L, were significantly up-regulated in both pre- and post-treatment specimens obtained from "non-responders" when compared to samples obtained from those from "responders" (Table 1). Similarly, genes with differentially expressed exons (novel transcriptional hybrids) were identified as being up-regulated in biopsies of the "non-responders" as opposed to the "responders", like CAPN3, RHBG, MFAP5, DPYS, GTF2I. The top 20 genes differentially expressed and ranked according to level of significance (highest to lowest) are shown in Table 1.

In order to investigate possible genes associated with MEK inhibitor resistance, particular focus was placed on the DEAD-box helicase antigen DDX43. The expression of DDX43 was 60-fold higher in the "non-responders" compared to "responders". DDX43 has been reported to be highly expressed in many tumor types including melanoma when compared to normal tissues [16, 17, 19]. In order to validate the RNAseq results for DDX43, we performed real-time PCR and expanded our analysis to include 14 biopsy samples (6 "responders" and 8 "non-responders") for DDX43 expression at pre-treatment condition (FIG. 1A). Patients who responded to therapy ("responders") had low expression of DDX43. In contrast, DDX43 was highly expressed in the "non responders", and there was a statistically significant association with poor outcome in these patients (p=0.045). Similarly, protein levels of DDX43 were low in "responders" at baseline, and slightly induced post-selumetinib treatment (FIG. 1B), while it was highly expressed in "non responders" regardless of treatment.

DDX43 is Highly Expressed in UM Cell Lines with Acquired Resistance to Selumetinib.

Figure 2A:
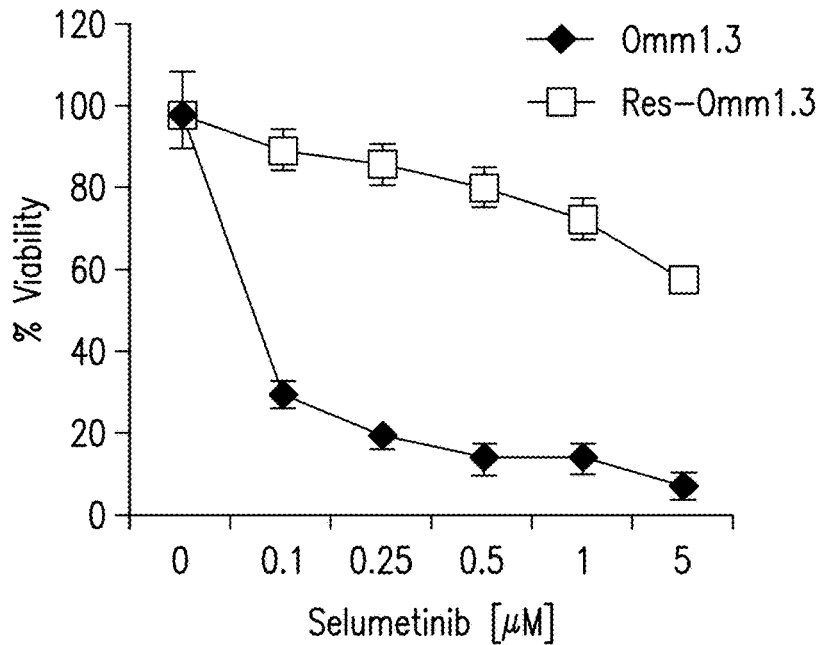

To explore mechanisms of drug resistance, MEKi-resistant GNAQ-mutant cell lines were generated by exposing the cells to increasing concentrations of selumetinib for at least four weeks and routinely grown in 1 µM selumetinib, without clonal selection. After continuous exposure, the cell lines Res-Omm1.3 and Res-Mel270 became resistant to selumetinib compared to their parental cells Omm1.3 and Mel270 (FIG. 2A, B). The resistant cells showed IC50 that were 10 fold higher than their sensitive counterparts. Furthermore, these cells showed cross resistance to the MEK inhibitor PD0325901 and GSK1120212 (FIG. 7).

Figure 2B:
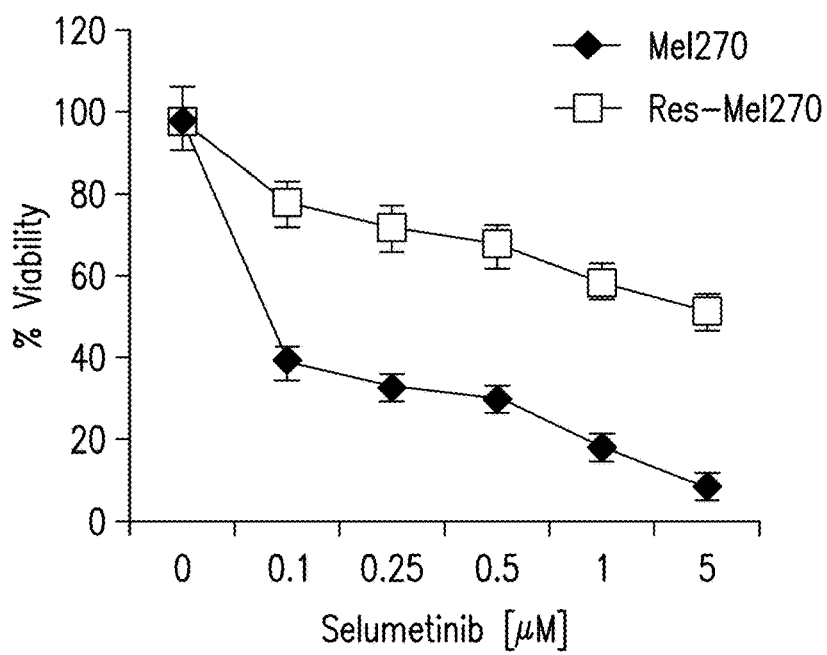
Figure 2C:
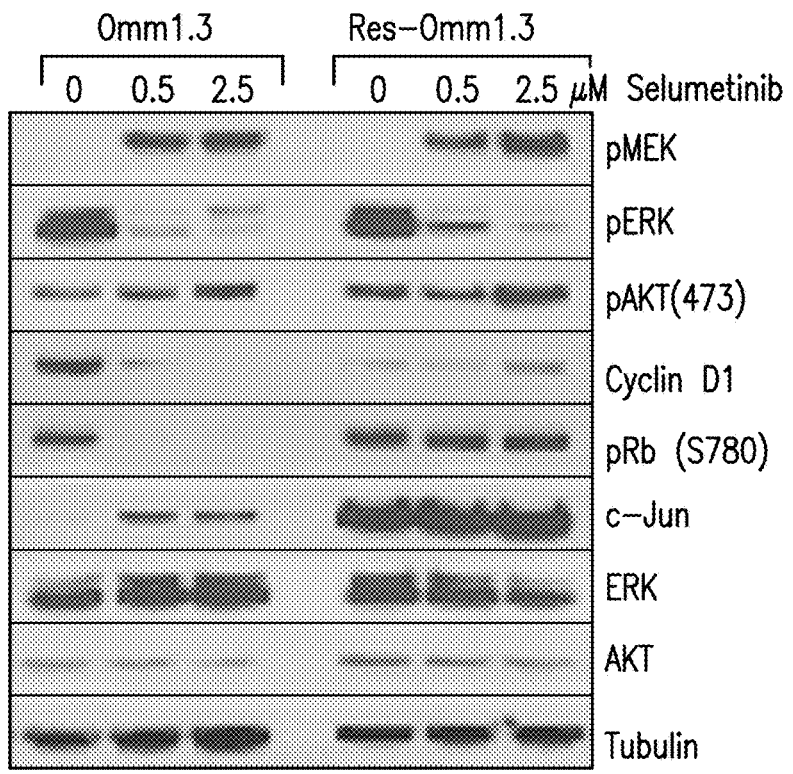
Figure 2D:
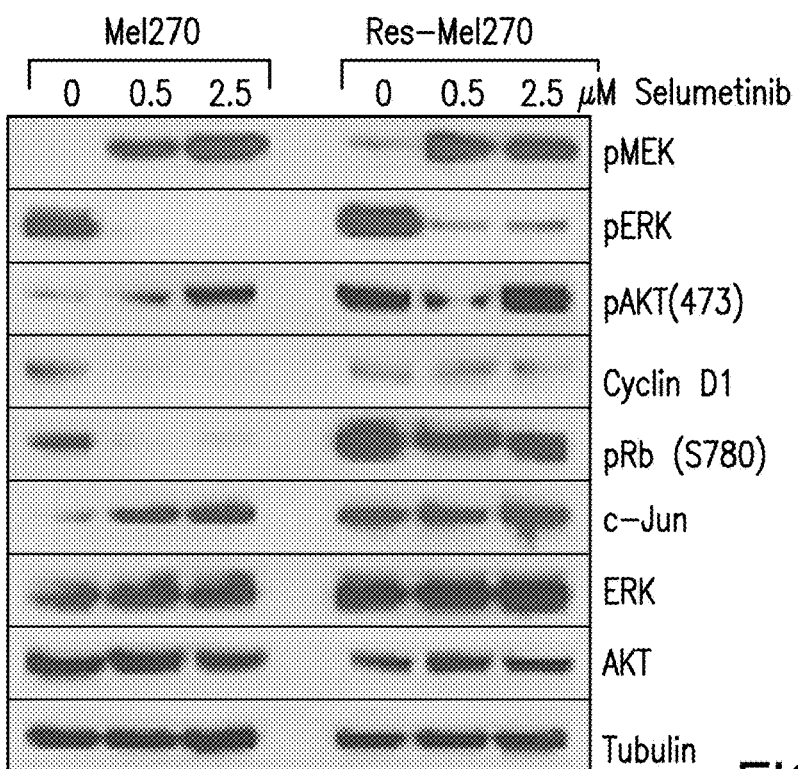

The resistant cells showed no cell cycle arrest with increasing doses of selumetinib, compared to the dose-dependent arrest in G1 population in the parental cells (FIG. 8). The expression level and phosphorylation status of different components of the MAPK pathway were then examined by immunoblotting. In parental Omm1.3 and Mel270 cells, treatment with selumetinib caused a decrease in pERK, cyclin D1 and phospho-retinoblastoma protein (pRB) (FIGS. 2C and 2D). Res-Omm1.3 and Res-Mel270 cells were maintained in drug-free media for 24 h, and when treated again their pERK decreased, while cyclin D1 and pRB remained unchanged. Of note, selumetinib induced pMEK in both parental and resistant cells, suggesting that MEK feedback mechanisms are still intact in the resistant cells, while downstream signaling is de-regulated, with low but sustained expression of cyclin D1 and constitutive activation of pRB. Higher levels of pAKT were observed at baseline and with the treatments, when compared to the parental cells (FIGS. 2B and 2D). It has been reported that mutant GNAQ signals to both ERK and AKT [26], and the increase in pAKT suggests that the GNAQ-mutant resistant cells adapt to MEK inhibition by increasing the flux through the PI3K/AKT pathways to maintain cell proliferation. We have also reported that c-Jun is uniquely upregulated by selumetinib in GNAQ mutant cells, as opposed to BRAF-mutant or wild-type cells, and it mediated intrinsic resistance to selumetinib [7]. In addition, Little et al. reported an increase in c-Jun in colorectal cancer cells with acquired resistance to selumetinib [14]. Indeed, c-Jun was induced by selumetinib in the parental cells and highly expressed in Res-Omm1.3 and Res-Mel270 resistant cells.

Finally, the cell lines were analyzed for DDX43 expression. These cells showed high levels of DDX43 protein compared to their parental cells (FIG. 3A), and the expression did not change with treatments, or over time (FIG. 3B). The increased expression of DDX43 was also confirmed at the mRNA levels in the resistant cell lines (FIG. 9). Since DDX43 was reported to regulate NRAS translation [20], RAS levels were analyzed in all the cell lines. Pan-RAS expression was slightly induced by selumetinib in the parental cells at higher doses (FIG. 3A) and over time (FIG. 3B), while it was constitutively expressed in both resistant cell lines (FIG. 3A, B). This has important implications as RAS regulates multiple pathways [27, 28] and could explain the increased flux into both the ERK and AKT in the resistant cells.

Next, experiments were performed to determine whether RAS protein levels correlated with RAS activity, by pull down assays. In the parental Omm1.3 and Mel270 cells, basal RAS expression and activity were relatively low and were slightly induced by the selumetinib treatment (FIG. 3C). However, RAS activation was temporary, and it returned to normal levels after 24 hours of drug removal. This activation of RAS is possibly mediated by the down-regulation of the Sprouty proteins by MEK inhibition as reported [29]. It has also been shown that GNAQ mutant cells have an elevated Spry2 expression that is downregulated by selumetinib treatment ([30] and FIG. 10). In contrast, RAS expression and activity was elevated in the resistant cells, and it remained active even when selumetinib was removed for up to 48 and 96 hours in Res-Mel270 and Res-Omm1.3 cells, respectively (FIG. 3C). In these cells Spry2 was also downregulated by the treatment or not expressed (FIG. 10), which could contribute to the elevated activity of RAS, but not to its expression. Other possible mechanisms of acquired resistance to MEK inhibition were explored by performing genomic sequencing and/or by FISH analysis of MEK, KRAS, NRAS, HRAS, but neither mutations nor gene amplification of the oncogene GNAQ or RAS proteins were observed. Assays failed to detect activation of receptor tyrosine kinases (RTK) resulted also negative.

Acquired Resistance to Selumetinib is Mediated by DDX43-Mediated RAS Expression in GNAQ Mutant Cells.

In order to determine whether DDX43 regulates RAS expression, DDX43 was silenced in the resistant cells using two siRNA sequences (siDDX43-1, FIG. 4; and siDDX43-2, FIG. 11). Downregulation of DDX43 in both resistant cell lines corresponded to decreased expression of KRAS, NRAS, HRAS and the downstream effectors pERK, pAKT and c-Jun (FIG. 4A). DDX43 downregulation also induced PARP cleavage (FIG. 4A), which corresponded to decreased cell viability of both the resistant cell lines (FIG. 4B), suggesting that DDX43 is required for sustained RAS expression and cell survival. DDX43 depletion did not affect RAS mRNA expression, as detected by real-time PCR analysis (FIG. 12) as previously reported [20], nor RAS protein stability.

To further characterize these mechanisms of drug resistance, DDX43 was over-expressed in the parental cells. In these cells, DDX43 induced expression of RAS and pAKT, but not pERK (FIG. 4C). In addition, the parental cells overexpressing DDX43 became more resistant to selumetinib treatments, compared to mock cells (FIG. 4D), confirming that DDX43 renders cells resistant to the MEK inhibitor through RAS and AKT activation.

In order to confirm that the effects of DDX43 silencing are mediated by RAS downregulation, each RAS protein was directly downregulated in both sensitive and resistant cells by gene-specific siRNA. Interestingly, KRAS and HRAS knockdown caused downregulation of pERK, pAKT in all the cell lines (FIG. 5A, B), while NRAS did not (FIG. 5C). c-Jun was downregulated in cells depleted of KRAS and NRAS, while HRAS regulated expression of c-Jun in one of the resistant cell lines (Res-Mel270).

Figure 5A:
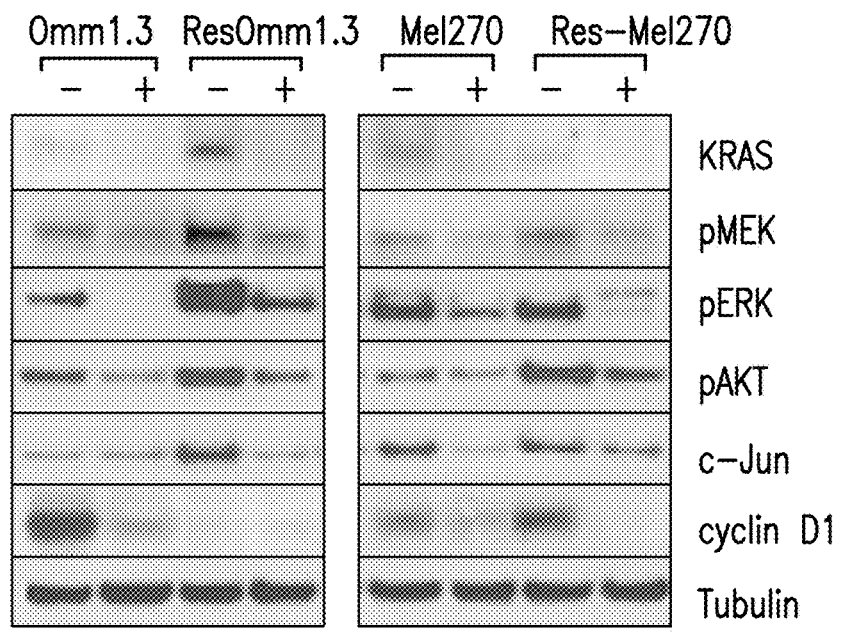
Figure 5B:
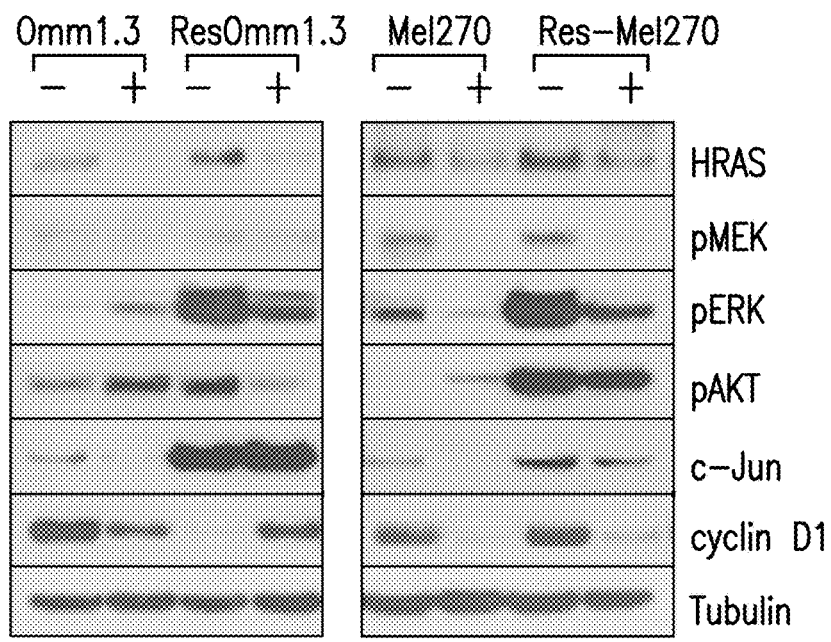
Figure 5C:
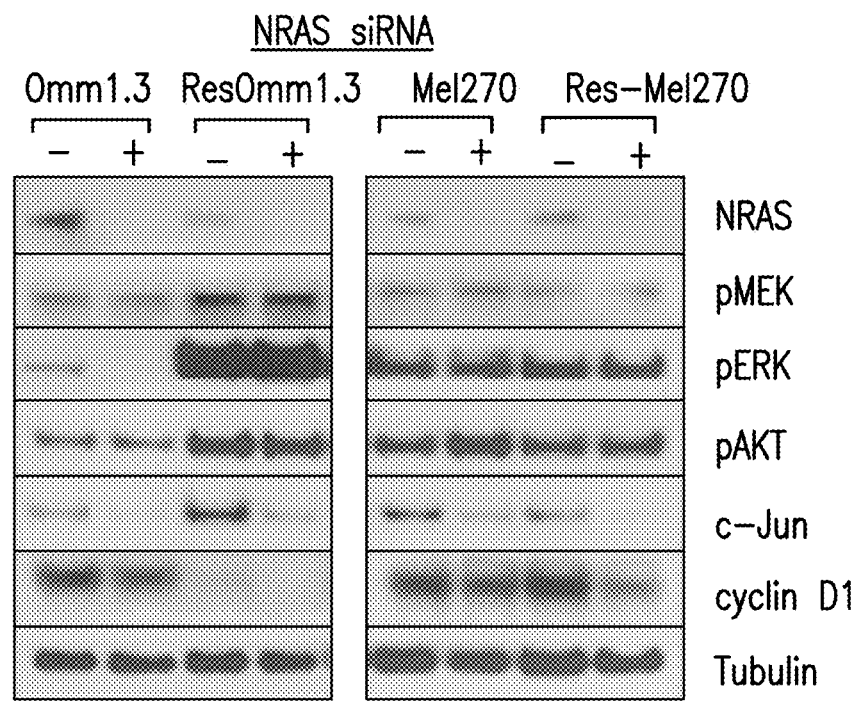
Figure 5D:
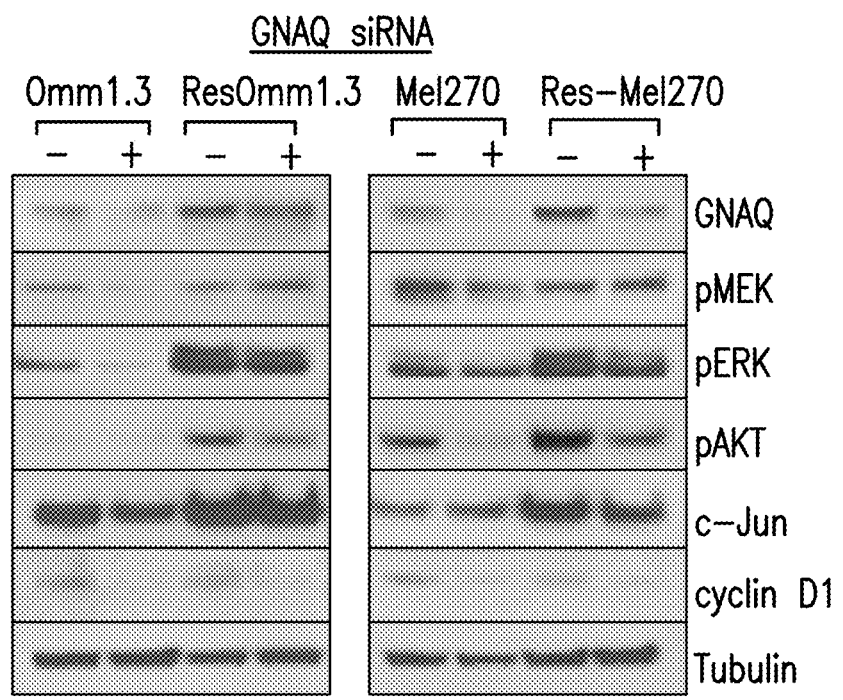

Since RAS proteins regulate signaling in the MEK-resistant cells, the contribution of mutant GNAQ on downstream signaling pathways was evaluated in these cells. GNAQ silencing inhibited pERK and pAKT in the parental cells as previously reported [26], while none or minimal inhibition was seen in the resistant cells (FIG. 5D). Expression of c-Jun was not affected by GNAQ siRNA in any of the cell lines.

Moreover, KRAS and HRAS downregulation decreased cell viability of the resistant cell lines, while NRAS had partial effects, and GNAQ had minimal effects (FIG. 6A, B).

These results indicate that KRAS and HRAS signal to MEK and AKT and mediate c-Jun expression in the resistant cells. This is also supported by the lack of inhibition of pMEK by GNAQ siRNA in the resistant cells but not in the sensitive cells (FIG. 5D), which suggests that mutant GNAQ loses its capacity to activate MEK in the resistant cells, while RAS proteins become the dominant mediators of cell signaling. This is further confirmed by the general resistance of these cells to inhibition of cell viability by GNAQ depletion (FIG. 6A), as opposed to the parental cells, which are sensitive to GNAQ silencing (26, 6).

AKT Inhibition Suppresses Cell Viability of Selumetinib-Resistant GNAQ Mutant Cells.

The increased RAS expression and activity mediates activation of downstream survival pathways, especially pAKT (FIG. 2C, D and FIG. 4C.) Accordingly the effects of the AKT inhibitor MK2206 (AKTi) were evaluated in these MEKi-resistant cell lines. Decreased viability was observed with AKTi in both Res-Omm1.3 and Res-Mel270 when compared to the parental lines (FIGS. 6B and C). This sensitivity to AKTi was sustained when combined with MEKi (FIGS. 6B and C), suggesting that AKT inhibition may be a means of overcoming MEKi-resistance

6.3 Discussion

The preliminary results of the single agent phase II study with selumetinib in patients with metastatic uveal melanoma appear promising with inhibition of pERK, suppression of cyclin D1, and partial radiologic responses [8].

However, acquired resistance to MEK inhibitors is common and undermines the efficacy of these treatments [12, 31]. Using a whole-transcriptome sequencing technology (RNA-seq) of paired tumor samples, and validation in cell lines with acquired MEK inhibitor-resistance, we identified DDX43 as a mediator of MEK resistance.

MEK resistant cells became sensitive to AKT inhibition, by overcoming MEK resistance and providing an alternative treatment for patient who fail a MEK inhibitor regiment. MEK resistance has been described in the setting of BRAF and RAS mutations, by amplification of the driving oncogene [14] or by dimerization of aberrantly spliced mutant BRAF [32]. Recently, Lito et al, have described that BRAF inhibitors cause relief of negative feedback with the activation of RAS and rebound of ERK activity [29].

A similar activation of RAS was induced by MEK inhibition in GNAQ mutant cells. This effect was possibly due to feedback activation, and it was reversible in cells exposed to the drug for a short period of time. On the contrary, cells continuously exposed to the MEK inhibitor exhibited sustained expression of DDX43 and RAS. DDX43 silencing decreased RAS expression and its downstream effectors pERK and pAKT, thus making DDX43 a novel mediator of MEK resistance that could represent a class effect to all MEK inhibitors.

DDX43 is a member of the D-E-A-D (Asp-Glu-Ala-Asp) box family of RNA helicases, which comprises more than 60 members [33]. Another member of this family, DDX5, regulates alternative splicing of HRAS [34], while DDX11 in involved in sister chromatin cohesion, and is essential for the survival of advanced melanoma [35]. Altered expression of DDX43 has been reported in other human tumors [36] [24]. For example, DDX43 has been identified as a tumor specific gene expressed in human sarcoma [16], and its expression has been reported as a biomarker of poor clinical outcome of breast cancer [37]. In chronic myeloid leukemia, DDX43 over-expression was associated with gene demethylation, and it correlated with advanced disease and poor outcome [18]. Finally, DDX43 was required for tumor cell proliferation of malignant melanoma-initiating cells through RAS protein expression [20]. In the experiments described herein, DDX43 has been associated with MEK resistance in uveal melanoma through the activation of RAS and downstream pathways. In particular, overexpression of DDX43 led to the activation of pAKT. It has been reported, in BRAF-mutant cutaneous melanoma, that basal and treatment-induced activation of AKT mediates resistance to selumetinib [38]. In the experiments described herein, the treatment with an AKT inhibitor alone or in combination with a MEK inhibitor seemed to overcome resistance in our cells.

7. REFERENCES

1. Gragoudas, E. S., et al., Survival of patients with metastases from uveal melanoma. Ophthalmology, 1991. 98(3): p. 383-9; discussion 390.
2. Kath, R., et al., Prognosis and treatment of disseminated uveal melanoma. Cancer, 1993. 72(7): p. 2219-23.
3. Edelhauser, G., et al., Fotemustine chemoembolization of hepatic metastases from uveal melanoma: a retrospective single-center analysis. AJR Am J Roentgenol, 2012. 199 (6): p. 1387-92.
4. Yonekawa, Y. and I. K. Kim, Epidemiology and management of uveal melanoma. Hematol Oncol Clin North Am, 2012. 26(6): p. 1169-84.
5. Onken, M. D., et al., Oncogenic mutations in GNAQ occur early in uveal melanoma. Invest Ophthalmol Vis Sci, 2008. 49(12): p. 5230-4.
6. Van Raamsdonk, C. D., et al., Frequent somatic mutations of GNAQ in uveal melanoma and blue naevi. Nature, 2009. 457(7229): p. 599-602.
7. Ambrosini, G., et al., Identification of unique MEK-dependent genes in GNAQ mutant uveal melanoma involved in cell growth, tumor cell invasion, and MEK-resistance. Clin Cancer Res, 2012. 18 (13): p. 1-10.
8. Carvajal R. D., A. G., Wolchok J. D., Chapman P. B., Dickson M. A., D'Angelo S. P. et al., Pharmacodynamic activity of selumetinib to predict radiographic response in advanced uveal melanoma. J Clin Oncol 2012. 30 ((suppl; abstr 3004)).
9. Adjei, A. A., et al., Phase I pharmacokinetic and pharmacodynamic study of the oral, small-molecule mitogen-activated protein kinase kinase 1/2 inhibitor AZD6244 (ARRY-142886) in patients with advanced cancers. J Clin Oncol, 2008. 26(13): p. 2139-46.
10. O'Neil, B. H., et al., Phase II study of the mitogen-activated protein kinase 1/2 inhibitor selumetinib in patients with advanced hepatocellular carcinoma. J Clin Oncol, 2011. 29(17): p. 2350-6.
11. Bennouna, J., et al., A Phase II, open-label, randomised study to assess the efficacy and safety of the MEK1/2 inhibitor AZD6244 (ARRY-142886) versus capecitabine monotherapy in patients with colorectal cancer who have failed one or two prior chemotherapeutic regimens. Invest New Drugs, 2011. 29(5): p. 1021-8.
12. Little, A. S., P. D. Smith, and S. J. Cook, Mechanisms of acquired resistance to ERK1/2 pathway inhibitors. Oncogene, 2012.

13. Corcoran, R. B., et al., BRAF gene amplification can promote acquired resistance to MEK inhibitors in cancer cells harboring the BRAF V600E mutation. Sci Signal, 2010. 3(149): p. ra84.
14. Little, A. S., et al., Amplification of the driving oncogene, KRAS or BRAF, underpins acquired resistance to MEK1/2 inhibitors in colorectal cancer cells. Sci Signal, 2011. 4(166): p. ra17.
15. Emery, C. M., et al., MEK1 mutations confer resistance to MEK and B-RAF inhibition. Proc Natl Acad Sci USA, 2009. 106(48): p. 20411-6.
16. Martelange, V., et al., Identification on a human sarcoma of two new genes with tumor-specific expression. Cancer Res, 2000. 60(14): p. 3848-55.
17. Adams, S. P., et al., Frequent expression of HAGE in presentation chronic myeloid leukaemias. Leukemia, 2002. 16(11): p. 2238-42.
18. Roman-Gomez, J., et al., Epigenetic regulation of human cancer/testis antigen gene, HAGE, in chronic myeloid leukemia. Haematologica, 2007. 92(2): p. 153-62.
19. Mathieu, M. G., et al., HAGE, a cancer/testis antigen with potential for melanoma immunotherapy: identification of several MHC class I/II HAGE-derived immunogenic peptides. Cancer Immunol Immunother, 2007. 56(12): p. 1885-95.
20. Linley, A. J., et al., The helicase HAGE expressed by malignant melanoma-initiating cells is required for tumor cell proliferation in vivo. J Biol Chem, 2012. 287(17): p. 13633-43.
21. Fuller-Pace, F. V., DExD/H box RNA helicases: multifunctional proteins with important roles in transcriptional regulation. Nucleic Acids Res, 2006. 34(15): p. 4206-15.
22. Linder, P. and E. Jankowsky, From unwinding to clamping—the DEAD box RNA helicase family. Nat Rev Mol Cell Biol, 2011. 12(8): p. 505-16.
23. Jarmoskaite, I. and R. Russell, DEAD-box proteins as RNA helicases and chaperones. Wiley Interdiscip Rev RNA, 2011. 2(1): p. 135-52.
24. Robert, F. and J. Pelletier, Perturbations of RNA helicases in cancer. Wiley Interdiscip Rev RNA, 2013.
25. Anders, S. and W. Huber, Differential expression analysis for sequence count data. Genome Biol, 2010. 11(10): p. R106.
26. Ambrosini, G., et al., Inhibition of Mutant GNAQ Signaling in Uveal Melanoma Induces AMPK-Dependent Autophagic Cell Death. Mol Cancer Ther, 2013. 12(50: 768-76.
27. Yamamoto, T., S. Taya, and K. Kaibuchi, Ras-induced transformation and signaling pathway. J Biochem, 1999. 126(5): p. 799-803.
28. Karnoub, A. E. and R. A. Weinberg, Ras oncogenes: split personalities. Nat Rev Mol Cell Biol, 2008. 9(7): p. 517-31.
29. Lito, P., et al., Relief of profound feedback inhibition of mitogenic signaling by RAF inhibitors attenuates their activity in BRAFV600E melanomas. Cancer Cell, 2012. 22(5): p. 668-82.
30. Ambrosini, G., et al., Identification of unique MEK-dependent genes in GNAQ mutant uveal melanoma involved in cell growth, tumor cell invasion, and MEK resistance. Clin Cancer Res, 2012. 18(13): p. 3552-61.
31. Poulikakos, P. I. and D. B. Solit, Resistance to MEK inhibitors: should we co-target upstream? Sci Signal, 2011. 4(166): p. pe16.
32. Poulikakos, P. I., et al., RAF inhibitor resistance is mediated by dimerization of aberrantly spliced BRAF (V600E). Nature, 2011. 480(7377): p. 387-90.
33. Umate, P., N. Tuteja, and R. Tuteja, Genome-wide comprehensive analysis of human helicases. Commun Integr Biol, 2011. 4(1): p. 118-37.
34. Camats, M., et al., P68 RNA helicase (DDX5) alters activity of cis- and trans-acting factors of the alternative splicing of H-Ras. PLoS One, 2008. 3(8): p. e2926.
35. Bhattacharya, C., X. Wang, and D. Becker, The DEAD/DEAH box helicase, DDX11, is essential for the survival of advanced melanomas. Mol Cancer, 2012. 11: p. 82.
36. Abdelhaleem, M., Over-expression of RNA helicases in cancer. Anticancer Res, 2004. 24(6): p. 3951-3.
37. Chan S., A.-F.T.M.A., McArdle S., Moseley P., Johnson C., Andrew R., HAGE (DDX43) protein expression as an independent biomarker of poor clinical outcome of breast cancer (BC) and potential as a therapeutic target for ER-negative BC. J Clin Oncol 2012. 30 (suppl; abstr 1013).
38. Gopal, Y. N., et al., Basal and treatment-induced activation of AKT mediates resistance to cell death by AZD6244 (ARRY-142886) in Braf-mutant human cutaneous melanoma cells. Cancer Res, 2010. 70(21): p. 8736-47.
39. Trapnell, C., et al., Transcript assembly and quantification by RNA-Seq reveals unannotated transcripts and isoform switching during cell differentiation. Nat Biotechnol, 2010. 28(5): p. 511-5.
40. GenBank Accesion No. NM_018665, *Homo sapiens* DEAD (Asp-Glu-Ala-Asp) box polypeptide 43 (DDX43), mRNA.
41. Chen, Q., et al., Aberrant hypomethylation of DDX43 promoter in myelodysplastic syndrome. Br. J. Haematol., 2012. 158 (2): p. 293-296.
42. Linley, A. et al., The helicase HAGE expressed by malignant melanoma-initiating cells is required for tumor cell proliferation in vivo. J. Biol. Chem., 2012. 287 (17): p. 13633-13643.
43. GenBank Accession No. XM_003986327.1.
44. GenBank Accession No. XM_518584.3.
45. GenBank Accession No. NM_001191044.1.
46. GenBank Accession No. XM_848647.1.
47. GenBank Accession No. NP_061135.
48. GenBank Accession No. XP_003986376.1.
49. GenBank Accession No. XP_518584.2.
50. GenBank Accession No. NP_001177973.1.
51. GenBank Accession No. XP_853740.1.
52. Mathieu, M. et al., HAGE, a cancer/testis antigen expressed at the protein level in a variety of cancers. Cancer Immunity. 2010. 10:p. 2.

Various publications are cited herein, the contents of which are hereby incorporated by reference in their entireties.

What is claimed is:

1. A method of treating a subject having a uveal melanoma comprising (i) determining whether an anti-cancer effect is unlikely to be produced in the cancer by a MEK inhibitor, comprising determining whether cells of the cancer contain an increased level of DDX43 mRNA and/or DDX43 protein relative to a normal value or normal values; and (ii) treating the subject with a therapeutic amount of a MEK inhibitor if the level of DDX43 mRNA and/or protein is not increased or (iii) treating the subject with a therapeutic amount of an AKT inhibitor where the level of DDX43 mRNA and/or protein is increased.

2. The method of claim 1, wherein the AKT inhibitor is selected from the group consisting of VQD-002, perifosine, miltefosine, AZD5363, and MK2206.

3. The method of claim 2, wherein the AKT inhibitor is MK2206.

4. The method of claim 1, wherein the MEK inhibitor is selected from the group consisting of selumetinib, trametinib, MEK162, PD-325901, XL518, and CI-1040.

5. The method of claim 4, wherein the MEK inhibitor is selumetinib.

6. The method of claim 1, wherein (iii) further comprises treating the subject with a therapeutic amount of an AKT inhibitor where the level of DDX43 mRNA and/or protein is increased by at least a factor of about 10, at least a factor of about 15, at least a factor of about 20, at least a factor of about 30, at least a factor of about 40, or at least a factor of about 50, relative to the normal value or normal values.

* * * * *